United States Patent
Weng et al.

(10) Patent No.: US 10,182,979 B2
(45) Date of Patent: Jan. 22, 2019

(54) BIODEGRADABLE MICROSPHERES

(71) Applicants: Regents of the University of Minnesota, Minneapolis, MN (US); EmboMedics, Inc., Golden Valley, MN (US)

(72) Inventors: Lihui Weng, Woodbury, MN (US); Jafar Golzarian, Plymouth, MN (US); Omid Souresrafil, Maple Grove, MN (US)

(73) Assignees: Regents of the University of Minnesota, Minneapolis, MN (US); EmboMedics, Inc., Maple Grove, MN (US)

( * ) Notice: Subject to any disclaimer, the term of this patent is extended or adjusted under 35 U.S.C. 154(b) by 0 days.

(21) Appl. No.: 15/466,301

(22) Filed: Mar. 22, 2017

(65) Prior Publication Data
US 2017/0273888 A1  Sep. 28, 2017

Related U.S. Application Data

(60) Provisional application No. 62/311,741, filed on Mar. 22, 2016.

(51) Int. Cl.
*A61K 8/73* (2006.01)
*A61K 8/02* (2006.01)
(Continued)

(52) U.S. Cl.
CPC .............. *A61K 8/736* (2013.01); *A61K 8/025* (2013.01); *A61K 8/731* (2013.01); *A61K 31/745* (2013.01);
(Continued)

(58) Field of Classification Search
CPC .................................................... A61Q 19/11
See application file for complete search history.

(56) References Cited

U.S. PATENT DOCUMENTS 4,758,223 A   7/1988  Rydell
5,514,379 A   5/1996  Weissleder et al.
(Continued)

FOREIGN PATENT DOCUMENTS

CN   1481907 A   3/2004
CN   1762332 A   4/2006
(Continued)

OTHER PUBLICATIONS

Barnett et al., "In Vitro Assessment of EmboGel and UltraGel Radiopaque Hydrogels for the Endovascular Treatment of Aneurysms," Journal of Vascular Interventional Radiology, Apr. 2009, 20:507-512.
(Continued)

*Primary Examiner* — Bethany P Barham
*Assistant Examiner* — Barbara S Frazier
(74) *Attorney, Agent, or Firm* — Shumaker & Sieffert, P.A.

(57) ABSTRACT

The present disclosure describes a plurality of microspheres that include carboxymethyl chitosan (CCN) crosslinked with carboxymethyl cellulose (CMC). The microspheres are biocompatible, bioresorbable, and biodegradable. The microspheres may be used in personal care products, such as, for example, toothpaste, topical pain relief products, topical antibiotic products, skincare products such as anti-wrinkle products, eczema products, skin scrubs, acne cleansers, exfoliators, body washes, soaps, pre-shave creams, or the like.

26 Claims, 20 Drawing Sheets

(51) Int. Cl.
A61K 31/745 (2006.01)
A61Q 11/00 (2006.01)
A61Q 19/00 (2006.01)
A61Q 19/08 (2006.01)

(52) U.S. Cl.
CPC .............. *A61Q 11/00* (2013.01); *A61Q 19/00* (2013.01); *A61Q 19/007* (2013.01); *A61Q 19/08* (2013.01); *A61K 2800/28* (2013.01)

(56) References Cited

U.S. PATENT DOCUMENTS

| | | | |
|---|---|---|---|
| 5,635,215 | A | 6/1997 | Boschetti et al. |
| 5,648,100 | A | 7/1997 | Boschetti et al. |
| 6,197,346 | B1 | 3/2001 | Mathiowitz et al. |
| 6,960,617 | B2 | 11/2005 | Omidian et al. |
| 7,407,646 | B2 | 8/2008 | Laurent et al. |
| 8,617,132 | B2 | 12/2013 | Golzarian et al. |
| 8,741,351 | B2 | 6/2014 | Vogel et al. |
| 8,936,795 | B2 | 1/2015 | Golzarian et al. |
| 2002/0012705 | A1 | 1/2002 | Domb |
| 2004/0071776 | A1 | 4/2004 | Boudy et al. |
| 2005/0263916 | A1 | 12/2005 | Lanphere et al. |
| 2006/0067883 | A1* | 3/2006 | Krom ................ A61K 51/1255 424/1.29 |
| 2006/0105014 | A1 | 5/2006 | Cruise |
| 2006/0165804 | A1 | 7/2006 | Lewis et al. |
| 2006/0199010 | A1 | 9/2006 | DiCarlo et al. |
| 2006/0210635 | A1 | 9/2006 | Laurent et al. |
| 2007/0014831 | A1 | 1/2007 | Sung et al. |
| 2007/0031467 | A1 | 2/2007 | Abrahams et al. |
| 2007/0148768 | A1 | 6/2007 | Liao et al. |
| 2007/0264310 | A1 | 11/2007 | Hissong et al. |
| 2008/0039890 | A1 | 2/2008 | Matson et al. |
| 2008/0041715 | A1 | 2/2008 | Lanphere et al. |
| 2009/0117196 | A1 | 5/2009 | Boschetti |
| 2011/0082427 | A1 | 4/2011 | Golzarian et al. |
| 2011/0142965 | A1* | 6/2011 | Walke .................... A61K 8/31 424/725 |
| 2013/0330292 | A1* | 12/2013 | Lei ........................ A61K 8/11 424/70.17 |
| 2014/0099374 | A1 | 4/2014 | Golzarian et al. |
| 2014/0171907 | A1 | 6/2014 | Golzarian et al. |
| 2014/0274945 | A1 | 9/2014 | Blaskovich et al. |
| 2014/0274954 | A1 | 9/2014 | Chellappan et al. |
| 2017/0273888 | A1 | 9/2017 | Weng et al. |

FOREIGN PATENT DOCUMENTS

| | | |
|---|---|---|
| CN | 1939316 A | 4/2007 |
| CN | 101125225 A | 2/2008 |
| CN | 101209354 A | 7/2008 |
| EP | 1508344 A1 | 2/2005 |
| EP | 1810698 A1 | 7/2007 |
| EP | 2626088 A1 | 8/2013 |
| EP | 2803370 A1 | 11/2014 |
| WO | 2009056602 A1 | 5/2009 |
| WO | 2009072146 A1 | 6/2009 |
| WO | 2011044236 A1 | 4/2011 |
| WO | 2014152488 A2 | 9/2014 |
| WO | 2015033093 A1 | 3/2015 |

OTHER PUBLICATIONS

Brennecka et al., "In Vivo Experimental Aneurysm Embolization in a Swine Model with a Liquid-to-Solid Gelling Polymer System: Initial Biocompatibility and Delivery Strategy Analysis," World Neurosurgery, Nov. 2012; 78(5):469-80 (Epublished Nov. 1, 2011).
Fatimi et al., "A New Injectable Radiopaque Chitosan-Based Sclerosing Embolizing Hydrogel for Endovascular Therapies," Acta Biomaterialia, Jul. 2012; 8(7):2712-21 (Epublished Apr. 2012).
Flandroy et al., "(D,L) Polylactide Microspheres as Embolic Agent," Neuroradiology, vol. 32, No. 4, Feb. 1990, pp. 311-315.
Grosso et al., "Transarterial Chemoembolization for Hepatocellular Carcinoma with Drug-Eluting Microspheres: Preliminary Results from an Italian Multicentre Study," Cardiovascular Interventional Radiology, vol. 31(6), Aug. 12, 2008, pp. 1141-1149.
Haijun et al., "Effects of Carboxymethylchitosan-carboxymethylcellulose Membrane on Extraneural Adhesion Formation and Peripheral Nerve Regeneration," Journal of Clinical Rehabilitative Tissue Engineering Research, vol. 13 (34), Aug. 20, 2009, 5 pp. (English Translation of Abstract Only.).
Kazekawa et al., "Newly Synthesized Liquid Embolization Material for Arteriovenous Malformation," Journal Clinical Neuroscience, Mar. 1998, 5:45-48.
Weng et al., "Bioresorbable Hydrogel Microspheres for Transcatheter Embolization: Preparation and in Vitro Evaluation," Laboratory Investigation, Jun. 15, 2011, 9 pp.
Kettenbach et al. "Drug-Loaded Microspheres for the Treatment of Liver Cancer: Review of Current Results", Cardiovasc Intervent Radiol (2008) 31:468-476 (Epublished Jan. 29, 2008).
Ko et al., "Preoperative Portal Vein Embolization with a New Liquid Embolic Agent," Radiology, May 2003, vol. 227, No. 2:407-413 (Epublished Mar. 13, 2003).
Kutlu et al, "Pulmonary Embolism After Penile Deep Dorsal Vein Embolization with n-butyl-2-cyanoacrylate and Lipiodol Mixture" European Journal Radiology Extra, Mar. 2004, 49(3):103-106.
Laccourreye et al., "Biodegradable Starch Microspheres for Cerebral Arterial Embolization," Journal of Clinical and Laboratory Research, vol. 28, No. 2, Feb. 1993, pp. 150-154.
Laurent, "Microspheres and Nonspherical Particles for Embolization," Techniques in Vascular and Interventional Radiology, vol. 10, No. 4, Dec. 1, 2007, 10 pages.
Liu et al., "A Study of Doxorubicin Loading Onto and Release from Sulfopropyl Dextran Ion-Exchange Microspheres," Journal of Controlled Release, vol. 77, Dec. 2001, pp. 213-224.
Liu YF, et al. Preparation and characterization of glutaraldehyde cross-linked 0-carboxymethylchitosan microspheres for controlled delivery of pazufloxacin mesilate. Int J Biol Macromol. Jun. 1, 2007 ;41 (1 )L87-93.
Mottu et al., "Iodine-Containing Cellulose Mixed Esters as Radiopaque Polymers for Direct Emoblization of Cerebral Aneurysms and Arteriovenous Malformations," Biomaterials, Jan. 2002, 23(1):121-131.
Nitta et al., "Gelatin Microspheres: Initial Clinical Experience for the Transcatheter Arterial Embolization," European Journal of Radiology, vol. 67, Issue 3, Sep. 2008, 536-540.
Ohta et al., "Degradable Gelatin Microspheres as an Embolic Agent: An Experimental Study in a Rabbit Renal Model," Korean J. Radiol 8(5), Oct. 2007, pp. 418-428.
Pollak et al., "The Use of Cyanoacrylate Adhesives in Peripheral Embolization," Journal of Vascular Interventional Radiology, Aug. 2001, 12:907-913.
Shi et al., "Therapeutic Embolization of Meningiomas with Onyx for Delayed Surgical Resection," Surgical Neurology, Nov. 2008, 70:478-481 (Epublished Feb. 8, 2008).
Silas et al., "Sclerosis of Postoperative Lymphoceles: Avoidance of Prolonged Catheter Drainage with Use of a Fibrin Sealant," Journal of Vascular Interventional Radiology, Nov. 2006, 17:1791-1795.
Su et al., "Histopathological studies of a New Liquid Embolization Method Using Estrogen-Alcohol and Polyvinyl Acetate: Experimental Evaluations with a Model of Cortical Arterial Cannulation in the Canine Brain," Surgical Neurology, Jul. 1991, vol. 36, No. 1:4-11.
Wang et al., "Preparation and Characterization of Pingyangmycin-loaded Bovine Serum Albumin Microspheres for Embolization Therapy," International Journal of Pharmaceutics, vol. 336, No. 2, May 24, 2007, pp. 361-366.
Weng et al., "In Vitro Assessment of an in Situ Gelable Hydrogel for Adjunct Endovascular Treatment of Abdominal Aortic Aneurysms," Journal of Vascular and Interventional Radiology, Abstract 346, Mar. 2012, 23(3): S139.
Wu et al., "Preparation and Drug Release Characteristics of Pingyangmycin-Loaded Dextran Cross-Linked Gelatin Microspheres for Embolization Therapy," Journal of Biomedical Materials Research, Part B, vol. 78B, Issue I, Jul. 2006, 56-62.

(56) References Cited

OTHER PUBLICATIONS

Weng et al., "Doxorubicin loading and eluting characteristics of bioresorbable hydrogel microspheres: in vitro study," International Journal of Pharmaceutics.

Weng et al., "In vitro and in vivo evaluation of biodegradable embolic microspheres with tunable anticancer drug release," Acta Biomaterialia, Elsevier, vol. 9, Issue 6, Jun. 2013, 12 pp.

International Campaign Against Microbeads in Cosmetics, accessed from www.beatthemicrobead.org on Jul. 2015, 4 pp.

Weng et al., "Calibrated Bioresorbable Microspheres as an Embolic Agent: An Experimental Study in a Rabbit Renal Model," HHS Public Access, PMC Oct. 4, 2016, 15 pp.

Kim et al., "MRI Visible Drug Eluting Magnetic Microspheres for Transcatheter Intra-Arterial Delivery to Liver Tumors," Theranostics, vol. 5, Issue 5, Feb. 7, 2015, 12 pp.

Kim et al., "Multimodal Imaging of Nanocomposite Microspheres for Transcatheter Intra-Arterial Drug Delivery to Liver Tumors," Scientific Reports, Jul. 13, 2016, 10 pp.

Weng et al., "Synthesis and in vitro evaluation of MRI visible resorable and loadable microspheres for arterial embolization," Abstract only submitted for the SIR Annual Scientific Meeting, downloaded Jan. 25, 2018, 2 pp.

Sommer et al., "Multimodal Visibility (Radiography, Computed Tomography, and Magnetic Resonance Imaging) of Microspheres for Transarterial Embolization Tested in Porcine Kidneys," Investigative Radiology, vol. 48, No. 4, Apr. 2013, 10 pp.

\* cited by examiner

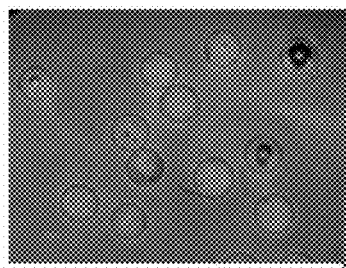
FIG. 5B
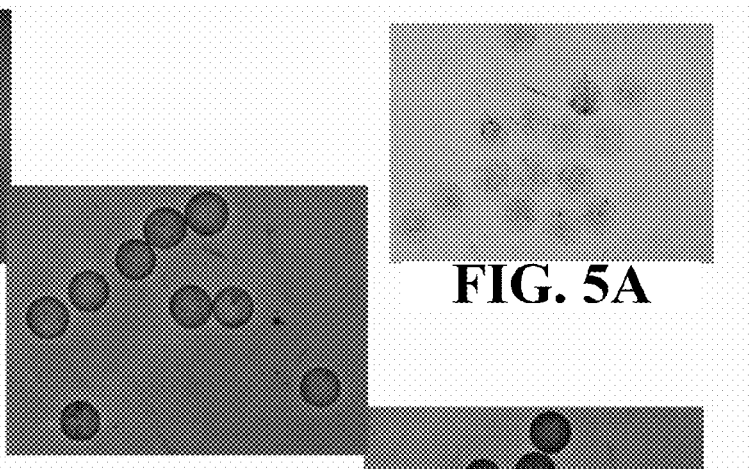
FIG. 5A
FIG. 5C
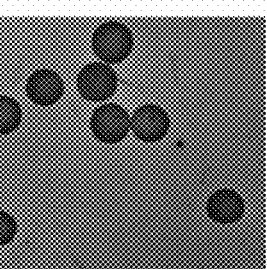
FIG. 5D
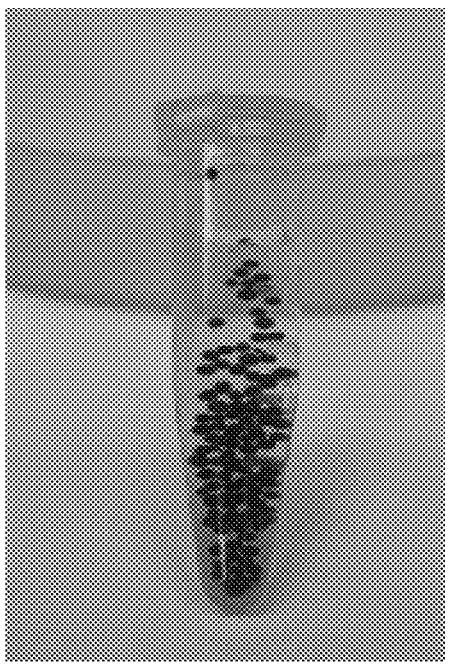
FIG. 5E
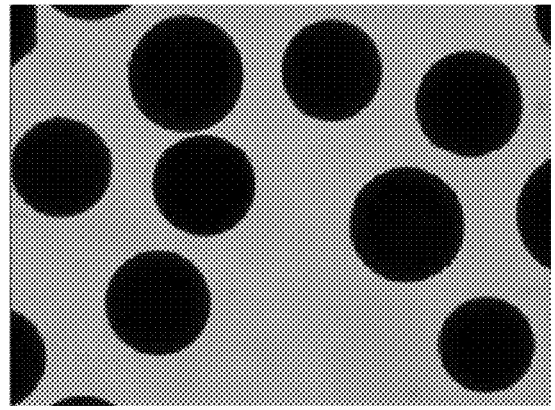
FIG. 5F

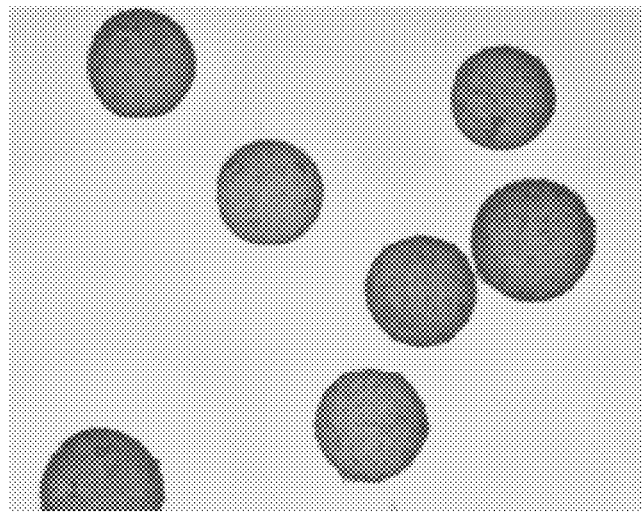
FIG. 6A
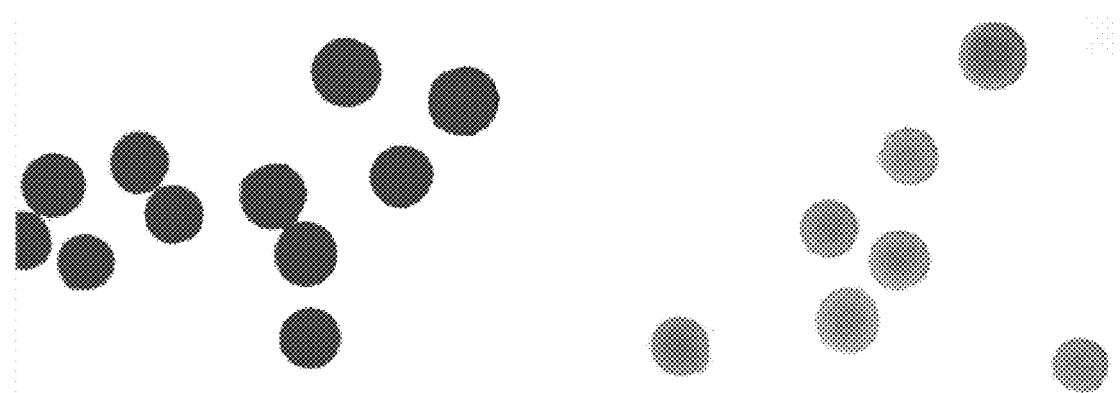
FIG. 6B  FIG. 6C

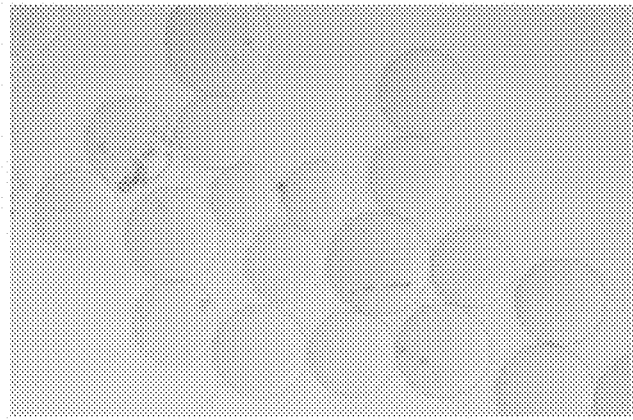
FIG. 18
FIG. 19A  FIG. 19B
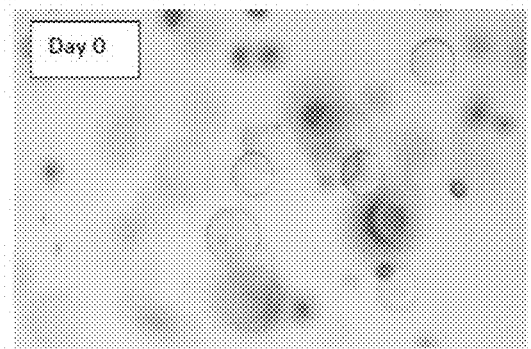 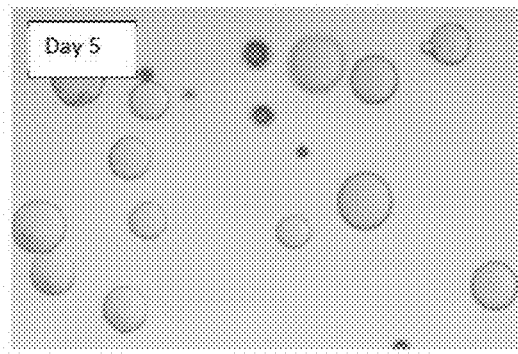
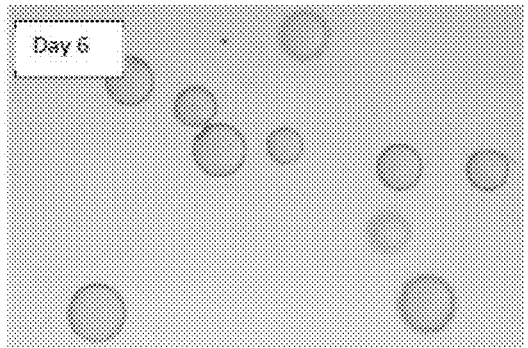 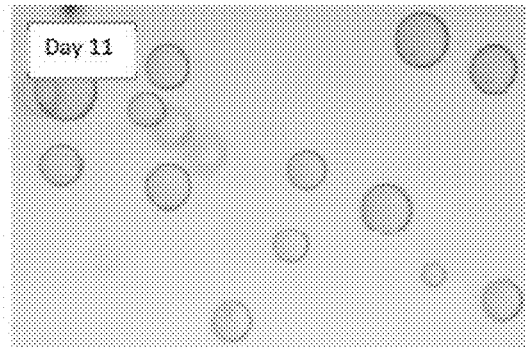
FIG. 19C  FIG. 19D

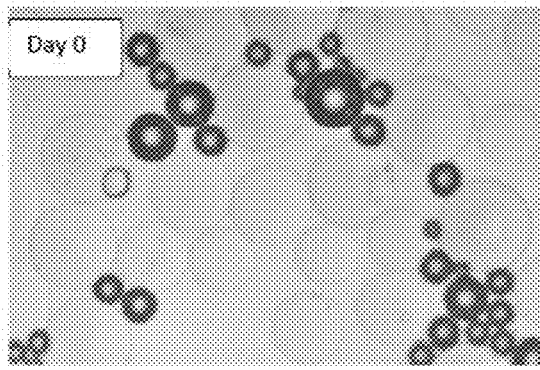
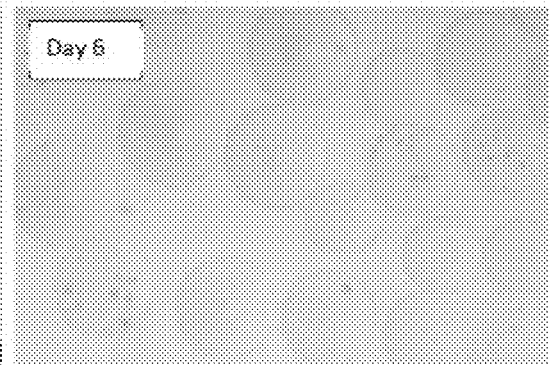
FIG. 21A  FIG. 21B
FIG. 22A  FIG. 22B
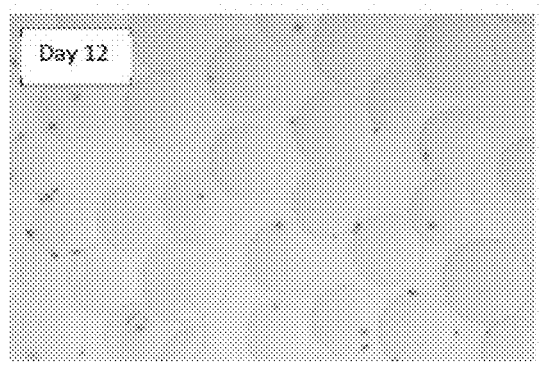
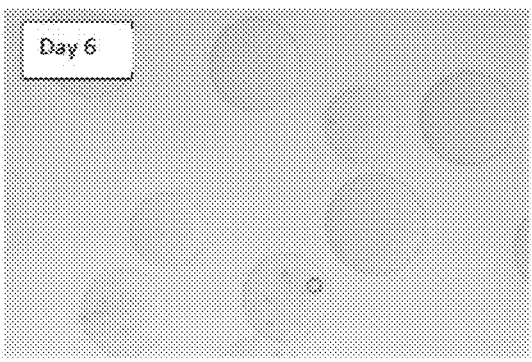
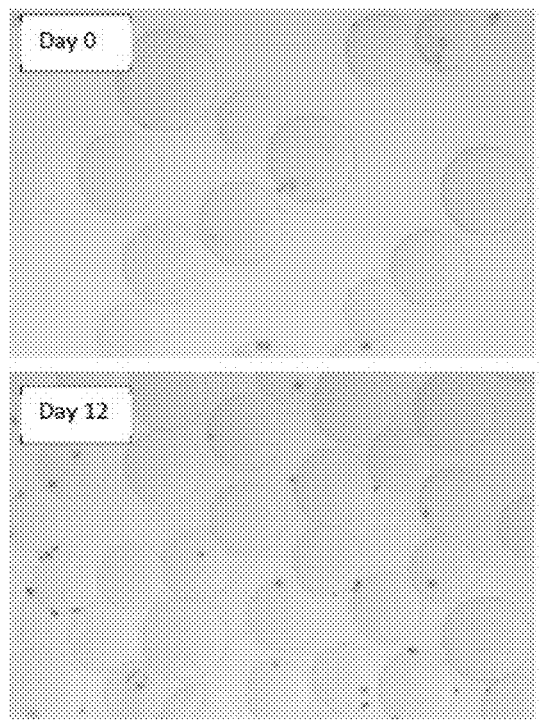
FIG. 22C

FIG. 23A
FIG. 23B
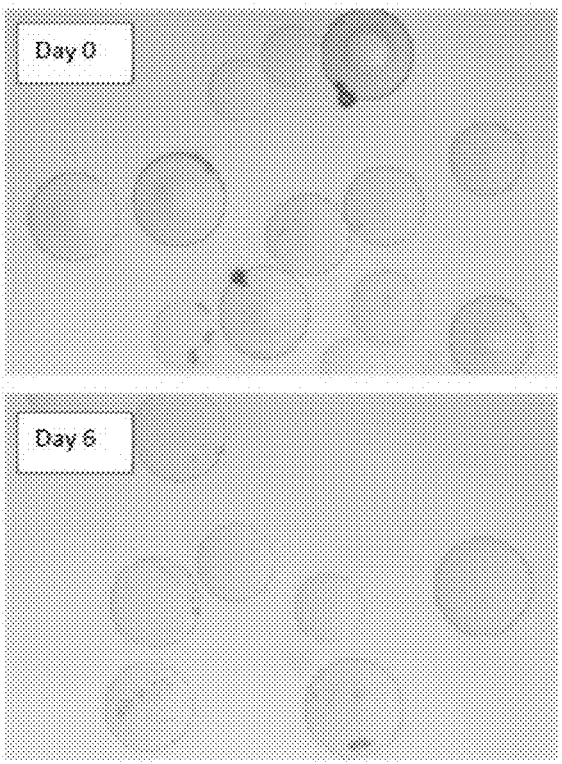
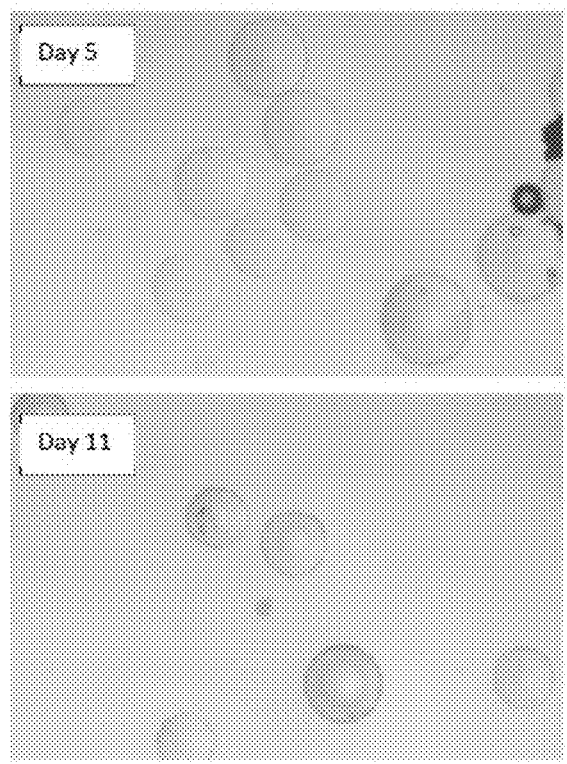
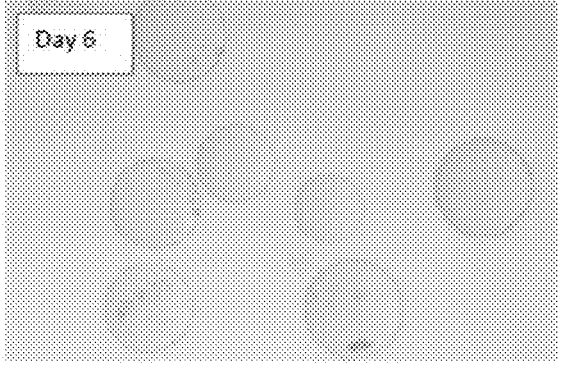
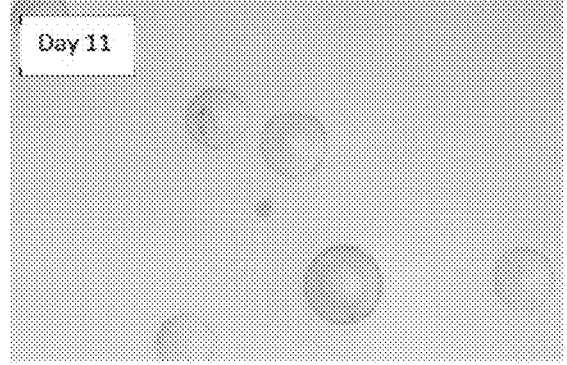
FIG. 23C
FIG. 23D

BIODEGRADABLE MICROSPHERES

This application claims the benefit of U.S. Provisional Application No. 62/311,741, filed Mar. 22, 2016, entitled, "BIODEGRADABLE MICROSPHERES," the entire content of which is incorporated herein by reference in its entirety. This application is related to U.S. Provisional Application No. 61/249,194, entitled, "EMBOLIZATION MICROSPHERES," filed on Oct. 6, 2009; International Patent Application No. PCT/US10/51629, which claims the benefit of U.S. Provisional Application No. 61/249,194; U.S. patent application Ser. No. 12/899,238, now U.S. Pat. No. 8,617,132, which is a national stage entry under 35 U.S.C. § 371 of International Patent Application No. PCT/US10/51629; and U.S. patent Ser. No. 14/098,443, which is a continuation of U.S. patent application Ser. No. 12/899,238. Each entire disclosure of each of these applications is incorporated herein by reference.

TECHNICAL FIELD

The disclosure relates to microspheres for use in personal care products, such as scrubs, soaps, and toothpaste.

BACKGROUND

Nonresorbable and non-biodegradable plastic microspheres have been added to facial scrubs, soaps, toothpastes, and other personal care products to act as an abrasive material to facilitate cleaning.

SUMMARY

In general, the disclosure is directed to microspheres including carboxymethyl chitosan (CCN) crosslinked with carboxymethyl cellulose (CMC). In some examples, the microspheres may have a diameter between about 40 micrometers (μm) and about 2200 μm. CCN and CMC each are biodegradable and biocompatible. In preparing the microspheres, CCN may be crosslinked by partially oxidized CMC, without use of a small molecule crosslinking agent. Because of this, the microspheres are expected to be biodegradable and biocompatible.

In some examples, the microspheres may be used in personal care products, such as toothpaste, skincare products, topical pain relief products, topical antibiotic products, anti-wrinkle products, eczema products, or the like. In some examples, the microspheres may be used as abrasive particles, which may facilitate cleaning of a surface, such as a tooth, skin, or the like. In some examples, the microspheres may additionally or alternatively include an active ingredient, such as an analgesic or other pain killer, an anti-acne agent, or the like. In this way, the microspheres may facilitate delivery of the active ingredient to the desired treatment site, and may release the active ingredient over time.

In some examples, the disclosure describes a personal care product that includes a plurality of microspheres including CCN crosslinked with CMC.

The personal care product may be a toothpaste. The toothpaste may include including a base material and a plurality of microspheres that include CCN crosslinked with CMC.

The personal care product may be an acne cleanser. The acne cleanser may include an active ingredient and a plurality of microspheres that include CCN crosslinked with CMC.

The personal care product may be an exfoliator product. The exfoliator product may include a base material and a plurality of microspheres that include CCN crosslinked with CMC.

The personal care product may be a body wash or facial wash. The wash may include a surfactant and a plurality of microspheres that include CCN crosslinked with CMC.

The personal care product may be a soap. The soap may include a derivative of a fatty acid and a plurality of microspheres that include CCN crosslinked with CMC.

The personal care product may be a pre-shave. The pre-shave may include water, a surfactant, and a plurality of microspheres that include CCN crosslinked with CMC.

The personal care product may be a topical pain relief product. The topical pain relief product may include an active ingredient and a plurality of microspheres that include CCN crosslinked with CMC.

The personal care product may be a topical antibiotic product. The topical antibiotic product may include at least one of an antibiotic, an antimicrobial, or an antifungal; and a plurality of microspheres. The plurality of microspheres include CCN crosslinked with CMC.

The personal care product may be an anti-wrinkle product. The anti-wrinkle product may include an active ingredient including at least one of retinol, a retinoid, niacinamide, an alpha hydroxyl acid, a beta hydroxyl acid, hyaluronic acid, hydroquinone, an antioxidant such as vitamin E or C, grape seed oil, a curcuminoid, a ceramide, a linoleic acid, a linolenic acid, or a phospholipid; and a plurality of microspheres. The plurality of microspheres include CCN crosslinked with CMC.

The personal care product may be an eczema treatment product. The eczema treatment product may include a moisturizer and a plurality of microspheres that include CCN crosslinked with CMC.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 5A-5F are light microscopy images illustrating loading of a dye into microspheres including CCN crosslinked with CMC.

FIGS. 6A-6C illustrate examples of microspheres according to an aspect of the disclosure after being loaded with various dyes.

FIG. 18 is an optical micrograph of microspheres including CCN crosslinked with CMC in normal saline.

FIGS. 19A-19D are optical micrographs of microspheres including CCN crosslinked with CMC mixed in an example hand soap at 30 minutes after mixing, about 5 days after mixing, about 6 days after mixing, and about 11 days after mixing, respectively.

FIGS. 21A and 21B are optical micrographs of microspheres including CCN crosslinked with CMC mixed in an example shave gel at 30 minutes after mixing and about 6 days after mixing, respectively.

FIGS. 22A-22C are optical micrographs of microspheres including CCN crosslinked with CMC mixed in an example toothpaste at 30 minutes after mixing, about 6 days after mixing, and about 12 days after mixing, respectively.

FIGS. 23A-23D are optical micrographs of microspheres including CCN crosslinked with CMC mixed in an example body wash at 30 minutes after mixing, about 5 days after mixing, about 6 days after mixing, and about 11 days after mixing, respectively.

DETAILED DESCRIPTION

Figure 1:
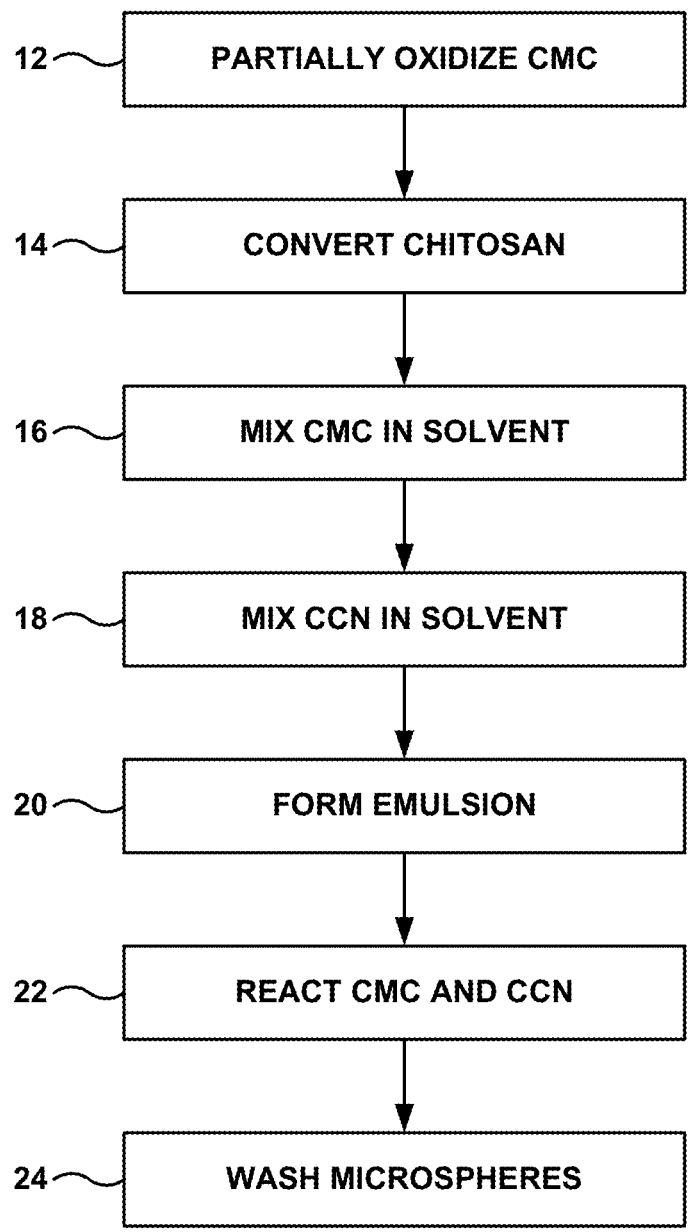
FIG. 1 is a flow diagram of an example technique for producing microspheres including carboxymethyl chitosan (CCN) crosslinked with carboxymethyl cellulose (CMC).

The present disclosure describes a plurality of microspheres that include carboxymethyl chitosan (CCN) crosslinked with carboxymethyl cellulose (CMC). The microspheres are biocompatible, bioresorbable, and biodegradable. The microspheres may be used in personal care products, such as, for example, toothpaste, topical pain relief products, topical antibiotic products, skincare products such as anti-wrinkle products, eczema products, skin scrubs, acne cleansers, exfoliators, body washes, pre-shave creams, or the like.

In accordance with examples of this disclosure, CCN and CMC may be crosslinked without use of a small molecule crosslinking agent to form microspheres that are substantially free of small molecule crosslinking agent. While use of a small molecule crosslinking agent facilitates crosslinking reactions, some small-molecule crosslinking agents may be toxic or have other adverse effects on cells or tissue in the body of the patient. By omitting small molecule crosslinking agents, such potential adverse effects may be avoided. In fact, in some examples, the crosslinking reaction between CMC and CCN may be carried out without a small molecule crosslinking agent and at relatively low temperatures (e.g., about 40° C.) in a water and oil emulsion. CCN is substantially non-toxic and biodegradable. Chitosan breaks down in the body to glucosamine, which can be substantially completely absorbed by a patient's body. Similarly, CMC is substantially non-toxic and biodegradable. Thus a crosslinked polymer formed by CCN and CMC is expected to the substantially non-toxic (i.e., biocompatible) and biodegradable (or bioresorbable). Additionally, because the crosslinked CCN and CMC microsphere is formed from two polymers, the mechanical properties, such as compressibility, of the crosslinked molecule are expected to be sufficient for use of the particles as abrasive agents.

The plurality of microspheres described herein may be used in a personal care product, such as a soap, a toothpaste, a topical pain relief product, a topical antibiotic product, a skincare product such as an anti-wrinkle product, an eczema treatment product, a skin scrub, an acne cleanser, an exfoliator, a body wash, a pre-shave product, and the like. The plurality of microspheres may be used as abrasive particles, which facilitate a cleaning action (e.g., scrubbing teeth to remove plaque, exfoliating dead skin cells, removing dirt or oil from skin, or the like). The plurality of microspheres may also or alternatively be loaded with active ingredients, such as anti-pain agents, anti-acne agents, antibiotics, or the like, and may facilitate delivery of the active agent to the target location. Because the plurality of microspheres are biocompatible and biodegradable, the microspheres may be acceptable for use in personal care products, and may degrade after use, which may reduce environmental contamination by the microspheres.

In some examples, the plurality of microspheres may have a mean or median diameter between about 40 μm and about 2200 μm. In some examples, the plurality of microspheres may have a mean or median diameter of less than about 2000 μm, microspheres with a mean or median diameter of between about 100 μm and about 1200 microspheres with a mean or median diameter of between about 100 μm and about 300 μm, microspheres with a mean or median diameter of between about 300 μm and about 500 microspheres with a mean or median diameter of between about 500 μm and about 700 μm, microspheres with a mean or median diameter of between about 700 μm and about 900 μm, microspheres with a mean or median diameter of between about 900 μm and about 1200 μm, or microspheres with a mean or median diameter of between about 1600 μm and about 2200 μm. In some examples, the diameter of the microspheres may be measured using optical microscopy, approximated using one or more sieves, or the like.

In some examples, the plurality of microspheres may be incorporated in a toothpaste. The microspheres may be used as abrasives in the toothpaste, which facilitate plaque and calculus or tartar removal from teeth.

Toothpaste may include a base material and the plurality of microspheres. In some examples, the base material may include a solvent, such as water. For example, the toothpaste may include up to about 50% water.

In some toothpastes, the base material also may include a fluoride source. A fluoride source releases fluoride, which may reduce or prevent cavities. The fluoride source may include, for example, sodium fluoride (NaF), stannous fluoride ($SnF_2$), sodium monofluorophosphate ($Na_2PO_3F$), olaflur (N,N,N'-tris(2-hydroxyethyl)-N'-octadecylpropane-1,3-diamine dihydrofluoride), or the like. In some examples, the toothpaste may include between about 1,000 parts per million (ppm) fluoride and about 1,500 ppm fluoride, such as between about 1,000 ppm fluoride and about 1,100 ppm fluoride, or between about 1,350 ppm fluoride and about 1,500 ppm fluoride.

In some examples, the base material may include a surfactant. The surfactant may facilitate foaming of the toothpaste during brushing. This may facilitate removal from teeth of plaque and tartar or calculus that has been loosened by the plurality of microspheres or bristles of the toothbrush. In some examples, the surfactant may include sodium lauryl sulfate (SLS), polyethylene glycol, cocamidopropyl betaine, or the like.

In some examples, the base material may include an antibacterial agent, which may reduce or prevent gingivitis, reduce tartar, or reduce bad breath. In some examples, the antibacterial agent may include triclosan (5-chloro-2-(2,4-dichlorophenoxy)phenol), zinc chloride, or the like.

In some examples, the base material may include a flavorant. A flavorant may include, for example, peppermint, spearmint, wintergreen, anise oil, bubblegum, cinnamon, orange, or the like. In some examples, toothpaste may include a colorant, such as a dye.

In some examples, the base material may include a remineralizer, which may facilitate reformation of tooth enamel. Remineralizers include, for example, hydroxyapatite, a calcium phosphate, or the like.

In some examples, the base material may include an anti-drying agent. An anti-drying agent may reduce or substantially prevent drying of toothpaste to a powder (e.g., after manufacture and prior to use). The anti-drying agent may include a sugar alcohol, such as, for example, glycerol, sorbitol, xylitol, derivatives thereof, or the like.

In some examples, the base material may include a desensitizing agent, which may reduce sensitivity of teeth to heat, cold, or the like. Desensitizing agents may include, for example, strontium chloride, potassium nitrate, or the like.

In some examples, the base material may include a whitening agent, such as peroxide, sodium tripolyphosphate, or the like.

In some examples, the base material may include a thickener, such as xanthan gum or the like.

The plurality of microspheres includes (CCN) and (CMC). The microspheres are biocompatible, bioresorbable, and biodegradable. CCN and CMC may be crosslinked without use of a small molecule crosslinking agent to form microspheres that are substantially free of small molecule crosslinking agent. While use of a small molecule crosslinking agent facilitates crosslinking reactions, some small-molecule crosslinking agents may be toxic or have other adverse effects on cells or tissue in the body of the patient. By omitting small molecule crosslinking agents, such potential adverse effects may be avoided. In fact, in some examples, the crosslinking reaction between CMC and CCN may be carried out without a small molecule crosslinking agent and at relatively low temperatures (e.g., about 40° C.) in a water and oil emulsion.

CCN is substantially non-toxic and biodegradable. Chitosan breaks down in the body to glucosamine, which can be substantially completely absorbed by a patient's body. Similarly, CMC is substantially non-toxic and biodegradable. Thus a crosslinked polymer formed by CCN and CMC is expected to the substantially non-toxic (i.e., biocompatible) and biodegradable (or bioresorbable). Additionally, because the crosslinked CCN and CMC microspheres are formed from two polymers, the mechanical properties, such as compressibility, of the crosslinked molecule are expected to be sufficient for use of the particles as abrasive agents.

Hence, the plurality of microspheres may act as abrasive particles in the toothpaste, which may facilitate removal of plaque and tartar or calculus from teeth. Further details regarding the plurality of microspheres will be described below.

The personal care product also may be a product for external use, such as an acne cleanser, an exfoliator, a body wash or facial wash, a soap, a pre-shave, a topical pain relief product, a topical antibiotic product, an anti-wrinkle product, an eczema treatment product, or the like.

The plurality of microspheres may be utilized in an acne cleanser. An acne cleanser may include an active ingredient, the plurality of microspheres, and, optionally, one or more of a surfactant, an alcohol, a moisturizer, an antiseptic, an antioxidant, a chelating agent, a pH adjusting agent, water, an oil, a thickener, or the like.

The active ingredient may include, for example, salicylic acid, benzoyl peroxide, a sulfur compound, an antimicrobial such as chlorhexidine gluconate or benzalkonium chloride, or the like. In some examples, the active ingredient may be present in the acne cleanser in between about 0.1 wt. % and about 10 wt. %, such as 2 wt. %, 5 wt. %, or 10 wt. %.

The optional surfactant may include, for example, a nonionic surfactant, an anionic surfactant, a cationic surfactant, or an amphoteric surfactant. Example surfactants include stearic acid, stearyl alcohol, cetyl alcohol, triethanolamine, sodium methyl cocoyl taurate, cocamidopropyl betaine, self-emulsifying glycerin monostearate, polyethylene glycol monostearate, polyoxyethylene sorbitan monooleate, polyglycerin monostearate, polyoxyethylene cetyl ether, polyoxyethylated sterol, sorbitan monooleate, polyoxyethylated lanolin, lipophilic glycerin monostearate, polyoxyethylene hydrogenated castor oil, sodium cetylsulfate, sodium lauryl phosphate, triethanolamine palmitate, sodium stearyl phosphate, sodium polyoxyethylene lauryl phosphate, potassium palmitate, sodium N-acylglutamate, stearyldimethylbenzylammonium chloride, stearyltrimethylammonium chloride, lecithin, alkylaminoethylglycine chloride solution, or the like.

Example alcohols include, for example, cetyl alcohol, benzyl alcohol, menthol, or the like.

Example moisturizers include, for example, propylene glycol, dipropylene glycol, 1,3-butylene glycol, polyethylene glycol, glycerin, polyglycerin, sorbitol, sodium lactate, hyaluronic acid, collagen, muco-polysaccharide, neopentyl glycol dicaprate, cetyl alcohol, chondroitin sulfate, or the like.

Example thickeners include xanthan gum, sodium alginate, aluminum silicate, tragacanth gum, tragacanth starch, carbomer, acrylate and acrylamide copolymers, methyl cellulose, hydroxyethyl cellulose, carboxymethyl cellulose, cationized cellulose, C10-3-alkyl acrylate crosspolymer, cetyl alcohol, agar, or the like.

Example chelating agents include disodium edetate, ethylenediamine-tetraacetate, disodium ethylenediaminetetraacetic acid (disodium EDTA), pyrophosphate, hexametaphosphate, citric acid, tartaric acid, gluconic acid, or the like.

Example pH adjusting agents include sodium hydroxide, sodium citrate, triethanolamine, citric acid, boric acid, potassium hydrogen phosphate, or the like.

Example oils include, for example, petrolatum, paraffin wax, oils such as castor oil, olive oil, cacao oil, tsubaki oil, coconut oil, jojoba oil, grape seed oil, avocado oil, lauric acid, myristic acid, stearic acid, oleic acid, isostearic acid, behenic acid, cetanol, stearyl alcohol, hexyldecanol, octyldodecanol, lauryl alcohol, isopropyl palmitate, cholesterol oleate, or the like.

The plurality of microspheres may act as abrasive particles in the acne cleanser, which may facilitate removal of dirt, dead skin cells, oil, or the like, from skin, including pores. Further details regarding the plurality of microspheres will be described below.

In some examples, the active ingredient may be loaded into the microspheres. The microspheres may carry the active ingredient and release the active ingredient to the treatment site at which acne is being treated. In some examples, the active ingredient may be loaded into the microspheres during formation of the microspheres, i.e., during the crosslinking of the CCN with the partially oxidized CMC. In some such examples, the active ingredient may be deposited into an emulsion from which the microspheres are formed along with the CCN and partially oxidized CMC. As the microspheres form, the active ingredient may load into the microspheres. In other examples, the active ingredient may be loaded into the microspheres after formation of the microspheres. For example, the microspheres may be immersed in a solution of the active ingredient in a solvent, such as water, to load the active ingredient into the microsphere.

In some examples, the personal care product may be an exfoliator product. An exfoliator product may include a plurality of microspheres including CCN crosslinked with partially oxidized CMC. The exfoliator product may also include a base material. In some examples, the base material may include one or more of a surfactant, a moisturizer, a thickener, salicylic acid, a preservative, a chelating agent, a fragrance, or the like.

Salicylic acid may cause skin cells to be shed more easily, which may facilitate exfoliation.

The preservative may include, for example, phenoxyethanol, ethylhexylglycerin, methylchoroisothiazolinone, an antioxidant such as tocopheryl acetate, or the like.

The surfactant may include, for example, any of the surfactants described above with reference to the acne cleanser. The thickener may include, for example, any of the moisturizers described above with reference to the acne cleanser. The moisturizer may include, for example, any of the thickeners described above with reference to the acne cleanser. The chelating agent may include, for example, any of the chelating agents described above with reference to the acne cleanser.

In some examples, the plurality of microspheres may be used in a soap, body wash, or facial wash. A body wash or facial wash may include, for example, a solvent such as water, a surfactant, a moisturizer, a pH adjusting agent, a preservative, an antibacterial, an antifungal, a thickener, a fragrance, or the like, along with the plurality of microspheres.

The surfactant may include, for example, any of the surfactants described above with reference to the acne cleanser. The moisturizer may include, for example, any of the thickeners described above with reference to the acne cleanser. The pH adjusting agent may include, for example, any of the pH adjusting agents described above with reference to the acne cleanser. The thickener may include, for example, any of the moisturizers described above with reference to the acne cleanser. The preservative may include, for example, any of the preservatives described above with respect to the exfoliator product.

The antibacterial may include, for example, methylchoroisothiazolinone, benzyl benzoate, or the like.

The antifungal may include, for example, methylchoroisothiazolinone or the like.

A soap may include one or more of the ingredients of the body wash or facial wash described above. In addition, a soap may additionally include, for example, a derivative of a fatty acid. The fatty acid may include, for example, tallow, coconut oil, palm kernel oil, laurel oil, olive oil, rape seed oil, or the like.

In some examples, a pre-shave, which may be used prior to shaving body hair, may include the plurality of microspheres. A pre-shave helps lubricate the skin and reduce irritation from shaving. The plurality of microspheres may act as abrasives that help remove dirt, dead skin cells, oils, or the like from the skin prior to the shaving.

A pre-shave may include, for example, a solvent such as water, a surfactant, a preservative, a thickener, a moisturizer, a pH adjusting agent, salicylic acid, or the like.

The surfactant may include, for example, any of the surfactants described above with reference to the acne cleanser. The thickener may include, for example, any of the moisturizers described above with reference to the acne cleanser. The moisturizer may include, for example, any of the thickeners described above with reference to the acne cleanser. The preservative may include, for example, any of the preservatives described above with respect to the exfoliator product. The pH adjusting agent may include, for example, any of the pH adjusting agents described above with reference to the acne cleanser.

Salicylic acid may cause skin cells to be shed more easily, which may facilitate exfoliation.

The plurality of microspheres may also be used in a topical pain relief product, an antibiotic product, an anti-wrinkle product, or an eczema treatment product.

A topical pain relief product may include a plurality of microspheres and an active ingredient, which may be loaded in the plurality of microspheres. In some examples, the pain relief product may additionally, and optionally, at least one of a solvent such as water, a thickener, a surfactant, a pH adjusting agent, a moisturizer, a preservative, or the like.

The active ingredient may include, for example, an anesthetic, a pain reliever, an anti-inflammatory agent, an analgesic, or the like. For example, the active ingredient may include capsaicin; a salicylate; hydrocortisone; a counterirritant such as menthol, methylsalicylate, or camphor; pramoxine; or the like. Counterirritants may create a hot or cold sensation that distracts from pain.

The surfactant may include, for example, any of the surfactants described above with reference to the acne cleanser. The thickener may include, for example, any of the moisturizers described above with reference to the acne cleanser. The moisturizer may include, for example, any of the thickeners described above with reference to the acne cleanser. The preservative may include, for example, any of the preservatives described above with respect to the exfoliator product. The pH adjusting agent may include, for example, any of the pH adjusting agents described above with reference to the acne cleanser.

In some examples, the active ingredient may be loaded into the microspheres. The microspheres may carry the active ingredient and release the active ingredient to the treatment site at which pain is being treated. In some examples, the active ingredient may be loaded into the microspheres during formation of the microspheres, i.e., during the crosslinking of the CCN with the partially oxidized CMC. In some such examples, the active ingredient may be deposited into an emulsion from which the microspheres are formed along with the CCN and oxidized CMC. As the microspheres form, the active ingredient may load into the microspheres. In other examples, the active ingredient may be loaded into the microspheres after formation of the microspheres. For example, the microspheres may be immersed in a solution of the active ingredient in a solvent, such as water, to load the active ingredient into the microsphere.

A topical antibiotic product may include a plurality of microspheres and an active ingredient, which may be loaded in the plurality of microspheres. In some examples, the topical antibiotic product may additionally, and optionally, at least one of a solvent such as water, a thickener, a surfactant, a pH adjusting agent, a moisturizer, a preservative, an analgesic, or the like.

The active ingredient may include, for example, an antibiotic, antimicrobial, antifungal, or the like. For example, the active ingredient may include bacitracin, neomycin, polymyxin B, derivatives thereof, or the like.

The surfactant may include, for example, any of the surfactants described above with reference to the acne cleanser. The thickener may include, for example, any of the moisturizers described above with reference to the acne cleanser. The moisturizer may include, for example, any of the thickeners described above with reference to the acne cleanser. The preservative may include, for example, any of the preservatives described above with respect to the exfoliator product. The pH adjusting agent may include, for example, any of the pH adjusting agents described above with reference to the acne cleanser.

The analgesic may include, for example, pramoxine.

In some examples, the active ingredient may be loaded into the microspheres. The microspheres may carry the active ingredient and release the active ingredient to the treatment site at which infection is being treated or prevented. In some examples, the active ingredient may be loaded into the microspheres during formation of the microspheres, i.e., during the crosslinking of the CCN with the partially oxidized CMC. In some such examples, the active ingredient may be deposited into an emulsion from which the microspheres are formed along with the CCN and oxidized CMC. As the microspheres form, the active ingredient may load into the microspheres. In other examples, the active ingredient may be loaded into the microspheres after formation of the microspheres. For example, the microspheres may be immersed in a solution of the active ingredient in a solvent, such as water, to load the active ingredient into the microsphere.

An anti-wrinkle product may include a plurality of microspheres and an active ingredient, which may be loaded in the plurality of microspheres. In some examples, the anti-wrinkle product may additionally, and optionally, at least one of a solvent such as water, a thickener, a surfactant, a pH adjusting agent, a moisturizer, a preservative, or the like.

The active ingredient may include, for example, retinol, a retinoid, niacinamide, an alpha hydroxyl acid, a beta hydroxyl acid, hyaluronic acid, hydroquinone, an antioxidant such as vitamin E or C, grape seed oil, a curcuminoid, a ceramide, a linoleic acid, a linolenic acid, a phospholipid, or the like. Retinol is a derivative of vitamin A, which may open pores and smooth wrinkles. Niacinamide may reduce dark spots on skin. Hyaluronic acid is a moisturizer.

The surfactant may include, for example, any of the surfactants described above with reference to the acne cleanser. The thickener may include, for example, any of the moisturizers described above with reference to the acne cleanser. The moisturizer may include, for example, any of the thickeners described above with reference to the acne cleanser. The preservative may include, for example, any of the preservatives described above with respect to the exfoliator product. The pH adjusting agent may include, for example, any of the pH adjusting agents described above with reference to the acne cleanser.

In some examples, the active ingredient may be loaded into the microspheres. The microspheres may carry the active ingredient and release the active ingredient to the treatment site at which wrinkles are being treated. In some examples, the active ingredient may be loaded into the microspheres during formation of the microspheres, i.e., during the crosslinking of the CCN with the partially oxidized CMC. In some such examples, the active ingredient may be deposited into an emulsion from which the microspheres are formed along with the CCN and partially oxidized CMC. As the microspheres form, the active ingredient may load into the microspheres. In other examples, the active ingredient may be loaded into the microspheres after formation of the microspheres. For example, the microspheres may be immersed in a solution of the active ingredient in a solvent, such as water, to load the active ingredient into the microsphere.

The microspheres also may be used in an eczema treatment product. The eczema treatment product may include a moisturizer and the plurality of microspheres. In some examples, the eczema treatment product may additionally, and optionally, include at least one of a solvent such as water, a thickener, a surfactant, a pH adjusting agent, a preservative, or the like.

The moisturizer may include, for example, any of the thickeners described above with reference to the acne cleanser, may include colloidal oatmeal, or the like.

The surfactant may include, for example, any of the surfactants described above with reference to the acne cleanser. The thickener may include, for example, any of the moisturizers described above with reference to the acne cleanser. The preservative may include, for example, any of the preservatives described above with respect to the exfoliator product. The pH adjusting agent may include, for example, any of the pH adjusting agents described above with reference to the acne cleanser.

In some examples, the moisturizer may be loaded into the microspheres. The microspheres may carry the moisturizer and release the moisturizer to the treatment site at which eczema is being treated. In some examples, the moisturizer may be loaded into the microspheres during formation of the microspheres, i.e., during the crosslinking of the CCN with the partially oxidized CMC. In some such examples, the moisturizer may be deposited into an emulsion from which the microspheres are formed along with the CCN and oxidized CMC. As the microspheres form, the moisturizer may load into the microspheres. In other examples, the moisturizer may be loaded into the microspheres after formation of the microspheres. For example, the microspheres may be immersed in a solution of the moisturizer in a solvent, such as water, to load the moisturizer into the microsphere.

In some examples, the microspheres including CCN and CMC may be formed according to the technique illustrated in FIG. 1. Initially, CMC is at least partially oxidized to form partially oxidized CMC (12). One reaction that at least partially oxidizes CMC is illustrated in Reaction 1:

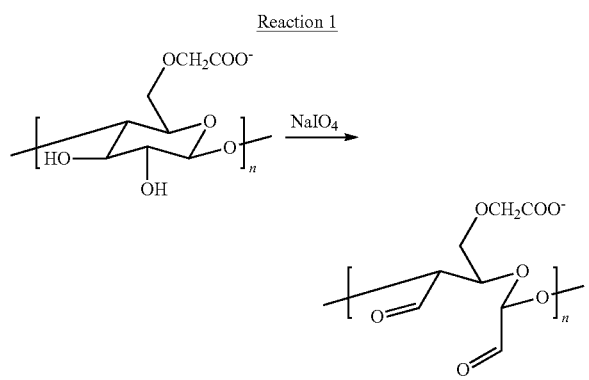

In Reaction 1, a single CMC monomer (repeating unit), which is part of a chain including n repeating units, is illustrated as reacting with $NaIO_4$ (sodium periodate to oxidize the C—C bond between carbon atoms bonded to hydroxyl groups to form carbonyl (more particularly aldehyde) groups. In some examples, the reaction may be carried out at about 25° C. Reaction 1 shows only a single repeating unit of the CMC polymer. In some examples, not all repeating units within the CMC polymer may be oxidized. For example, some repeating units may not be oxidized at all, and may still include two hydroxyl groups after Reaction 1 is performed. Other monomers may be oxidized, and may include two carbonyl groups, as illustrated in Reaction 1. The CMC may include a weight average molecular weight of between about 50,000 Daltons (Da; equivalent to grams per mole (g/mol)) and about 800,000 Da. In some examples, a weight average molecular weight of the CMC may be about 700,000 g/mol.

The degree of oxidation of the CMC may be affected by, for example, the molar ratio of $NaIO_4$ to CMC repeating units. In some examples, the molar ratio of $NaIO_4$ molecules to CMC repeating units may be between about 0.1:1 and about 0.5:1 ($NaIO_4$:CMC repeating unit). Particular examples of molar ratios of $NaIO_4$ molecules to CMC repeating units include about 0.1:1, about 0.25:1, and about 0.5:1. An increased molar ratio of $NaIO_4$ molecules to CMC repeating units may result in greater oxidation of the CMC, which in turn may lead to greater crosslinking density when CMC is reacted with CCN to form the microspheres. Conversely, a decreased molar ratio of $NaIO_4$ molecules to CMC repeating units may result in lesser oxidation of the CMC, which in turn may lead to lower crosslinking density when CMC is reacted with CCN to form the microspheres. In some examples, the crosslinking density may be approximately proportional to the degree of oxidation of the CMC. In some examples, a greater crosslinking density may lead to microspheres with greater mechanical strength (e.g., fracture strain).

CCN may be prepared by reacting chitosan to attach —$CH_2COO^-$ groups in place of one of the hydrogen atoms in an amine group or a hydroxyl group, as illustrated in Reaction 2 (14).

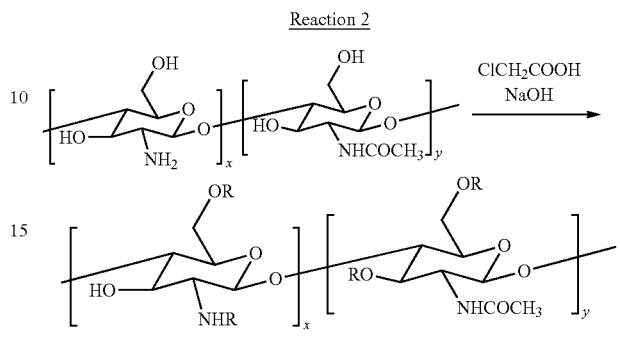

In the product of Reaction 2, each R is independently either H or —$CH_2COO^-$. Similar to oxidation of CMC shown in Reaction 1, the extent of the addition of the —$CH_2COO^-$ may affect the crosslink density when the CCN is reacted with the partially oxidized CMC to form the microspheres. The extent of the addition of the —$CH_2COO^-$ may be affected, for example, by the ratio of $ClCH_2COOH$ to CCN repeating units. In general, a greater ratio of —$CH_2COO^-$ to CCN repeating units may result in a greater extent of the addition of —$CH_2COO^-$, which a lesser ratio of —$CH_2COO^-$ to CCN repeating units may result in a lesser extent of the addition of —$CH_2COO^-$.

In some examples, the ratio of x:y in the CCN may be about 3:1 (i.e., monomers of "x" form about 75% of the chitosan and monomers of "y" form about 25% of the chitosan), although other ratios may also be used. In some examples, the chitosan starting material may have a molecular weight between about 190,000 g/mol and about 375,000 g/mol. In some examples, Reaction 2 may be performed by stirring the reaction mixture at 500 rpm for about 24 hours at about 25° C., followed by stirring the reaction mixture at 500 rpm for about 4 hours at about 50° C.

Once the partially oxidized CMC and the CCN have been prepared, each is mixed in a respective amount of a solvent, such as water (16), (18). For example, 0.1 milligram (mg) of partially oxidized CMC may be mixed in 5 milliliter (mL) of water to form a first 2% weight/volume (w/v) solution. Similarly, 0.1 mg of CCN may be mixed in 5 mL of water to form a second 2% w/v solution. Of course, solvents other than water may be used, and solutions having other concentrations of partially oxidized CMC or CCN, respectively, may be utilized. For example, saline or phosphate-buffered saline (PBS) may be utilized as alternative solvents. The solvent used in the partially oxidized CMC solution may be the same as or different than the solvent used in the CCN solution. The solutions may have concentrations of partially oxidized CMC or CCN between about 0.5% w/v and about 3% w/v. The concentration of the partially oxidized CMC solution may be the same as or different from the concentration of the CCN solution.

The first and second solutions may then be added to another solvent to form an emulsion (20). In some examples in which water is utilized as the solvent for the partially oxidized CMC and the partially oxidized CCN, the other solvent may be an oil, such as, for example, mineral oil. In some examples, the other solvent may include mixed therein a surfactant. One example of a suitable surfactant includes sorbitan monooleate, available under the tradename S6760 or Span® 80 from Sigma-Aldrich, St. Louis, Mo. In one example, 0.5 mL of sorbitan monooleate may be mixed in 50 mL of mineral oil, which is then mixed with the 5 mL 2% w/v solution of partially oxidized CMC and the 5 mL 2% w/v solution of CCN.

The emulsion is then left to allow the partially oxidized CMC and CCN to react (22) in a modified emulsion-crosslinking reaction. In some exmaples, the reaction time may be at least about 5 hours, such as 6 hours or at least 12 hours. In particular, an amino group on the CCN may react with an aldehyde group on the partially oxidized CMC to form a Schiff base (i.e., an N=C double bond) and crosslink the CMC and the CCN. One such crosslinking reaction is shown below in Reaction 3.

An extent of crosslinking between molecules of CMC and CCN may affect mechanical properties of the resulting microsphere. For example, a greater crosslinking density generally may provide greater mechanical strength (e.g., fracture strain), while a lower crosslinking density may provide lower mechanical strength (e.g., fracture strain). In some examples, the crosslinking density may be adjustable to provide a fracture strain of between about 70% and about 90%, as described below with respect to FIG. 7. The crosslinking density may also affect the degradation rate of the microsphere. For example, a greater crosslinking density may lead to a longer degradation time, while a lower crosslinking density may lead to a shorter degradation time. In some examples, the crosslink bonds may degrade through hydrolyzing of the C=N double bond.

Reaction 3

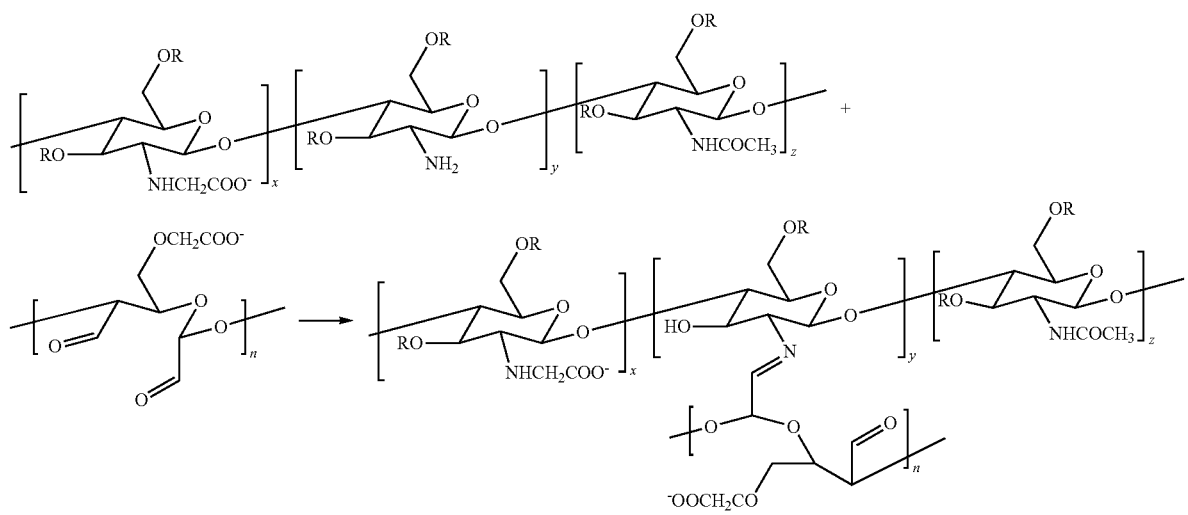

As discussed above, the crosslinking reaction of the CMC and CCN may proceed without use of a small-molecule crosslinking agent, such as glutaraldehyde. This may be advantageous, because in some examples, a small-molecule crosslinking agent may be toxic to a patient which uses products including the microspheres. In this way, the microspheres formed from CCN crosslinked with CMC may be substantially free of any small-molecule crosslinking agent.

In some examples, the crosslinking reaction between CMC and CCN may proceed under relatively benign conditions. For example, the crosslinking reaction may be carried out at ambient pressures and ambient temperatures (e.g., room temperature). In some examples, the reaction may be carried out at a temperature above ambient, such as, for example, 40° C. Example ranges of temperatures in which the crosslinking reaction may be performed include between about 20° C. and about 70° C., and at about 40° C. or about 65° C. In some examples, a lower reaction temperature may necessitate a longer reaction time to result in substantially similar diameter microspheres, or may result in smaller microspheres after a similar amount of time.

One advantage of performing the reaction at a temperature above room temperature may be the removal of water from the reaction mixture during the course of the reaction. For example, performing the crosslinking reaction at a temperature of about 65° C. may result in evaporation of water as the crosslinking reaction proceeds.

As described above, the crosslinking reaction between CMC and CCN is a modified emulsion-crosslinking reaction. In some examples, an emulsion-crosslinking reaction may be rate-limited by transport of the CMC and CCN molecules, and may play a role in the reaction product (the crosslinked CMC and CCN) being microspheres.

The size of the microspheres may be affected by reaction conditions, such as, for example, a stirring speed, a reaction temperature, a concentration of the CMC and CCN molecules in the reaction emulsion, an amount of mixing of the emulsion, or a concentration of the surfactant in the emulsion. For example, increasing the concentration of each of the CMC and CCN solutions from 1.5% w/v to 2% w/v while keeping the oxidation degree of CMC at about 25% (about 25 oxidized repeating units per 100 total repeating units), the stirring speed at 600 revolutions per minute (rpm), the temperature at about 50° C., the reaction time at about 12 hours, and the amount of Span 80 at about 0.3 mL/50 mL mineral oil, the average diameter of the microspheres may increase from about 600 μm to about 1100 μm. As another example, increasing the oxidation degree of CMC from about 10% to about 25% while keeping the concentration of each of the CMC and CCN solutions at about 1.5% w/v, the stirring speed at 600 rpm, the temperature at about 50° C., the reaction time at about 12 hours, and the amount of Span® 80 (a nonionic surfactant (sorbitane monooleate) available from Sigma-Aldrich® Co. LLC, St.

Louis, Mo.) at about 0.3 mL/50 mL mineral oil, the average diameter of the microspheres may increase from about 510 µm to about 600 µm.

In some examples, the reaction conditions may be selected to result in microspheres with a mean or median diameter between about 40 µm and about 2200 µm. In some examples, the reaction conditions may be selected to result in microspheres with a mean or median diameter of less than about 2000 µm, microspheres with a mean or median diameter of between about 100 µm and about 1200 µm, microspheres with a mean or median diameter of between about 100 µm and about 300 µm, microspheres with a mean or median diameter of between about 300 µm and about 500 microspheres with a mean or median diameter of between about 500 µm and about 700 µm, microspheres with a mean or median diameter of between about 700 µm and about 900 microspheres with a mean or median diameter of between about 900 µm and about 1200 µm, or microspheres with a mean or median diameter of between about 1600 µm and about 2200 µm. In some examples, the diameter of the microspheres may be measured using optical microscopy, approximated using one or more sieves, or the like.

Once the reaction has proceeded for a desired amount of time to produce microspheres with a desired mean or median diameter, the water in the emulsion may be substantially fully removed, if the water has not already been evaporated during the crosslinking reaction. The oil phase may then be removed, such as by decanting or centrifugation, and the microspheres may be washed (24). For example, the microspheres may be washed with Tween 80 solution (TWEEN® 80 is a polyethylene glycol sorbitan monooleate (polysorbate 80) surfactant available from Sigma-Aldrich® Co., LLC, St. Louis, Mo.). Finally, the microspheres may be stored in a liquid, such as water or saline, at a suitable temperature, such as between about 2° C. and about 8° C.

In some examples, the crosslinking reaction may produce a plurality of microspheres with diameters distributed about a mean or median. In some cases, it may be advantageous to isolate microspheres with diameters within a smaller range or microspheres with substantially a single diameter. In some examples, the microspheres may be separated according to diameter by wet sieving in normal saline through a sieve or sieves with predetermined mesh size(s).

Figure 2A:
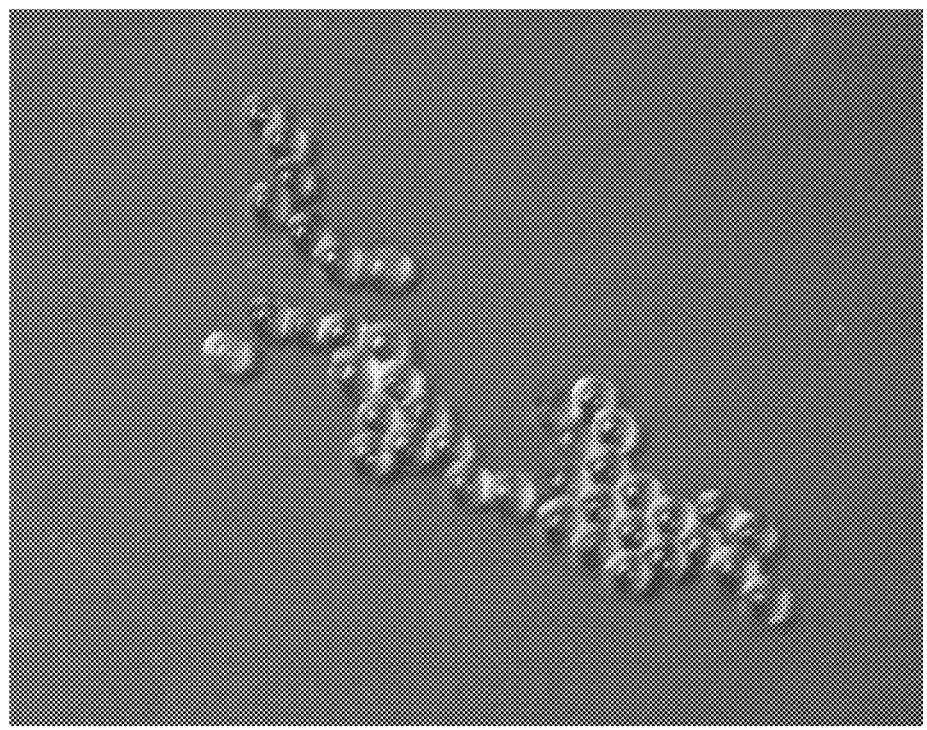
FIGS. 2A and 2B are a photograph and a light microscopy image, respectively, of microspheres in accordance with one aspect of the disclosure.
Figure 2B:
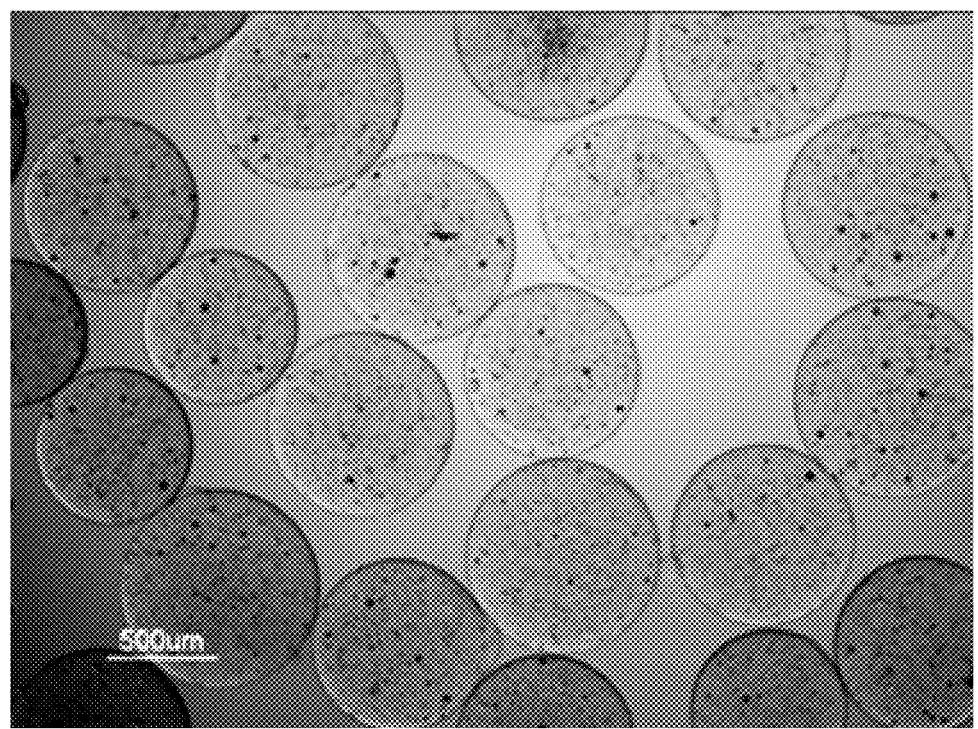

FIGS. 2A and 2B are a photograph and a light microscopy image of microspheres in accordance with one aspect of the disclosure. FIG. 2A illustrates that microspheres in accordance with the disclosure may be substantially spherical. FIG. 2B illustrates an example in which the diameter of the microspheres ranges from about 900 µm to about 1200 µm.

Figure 3:
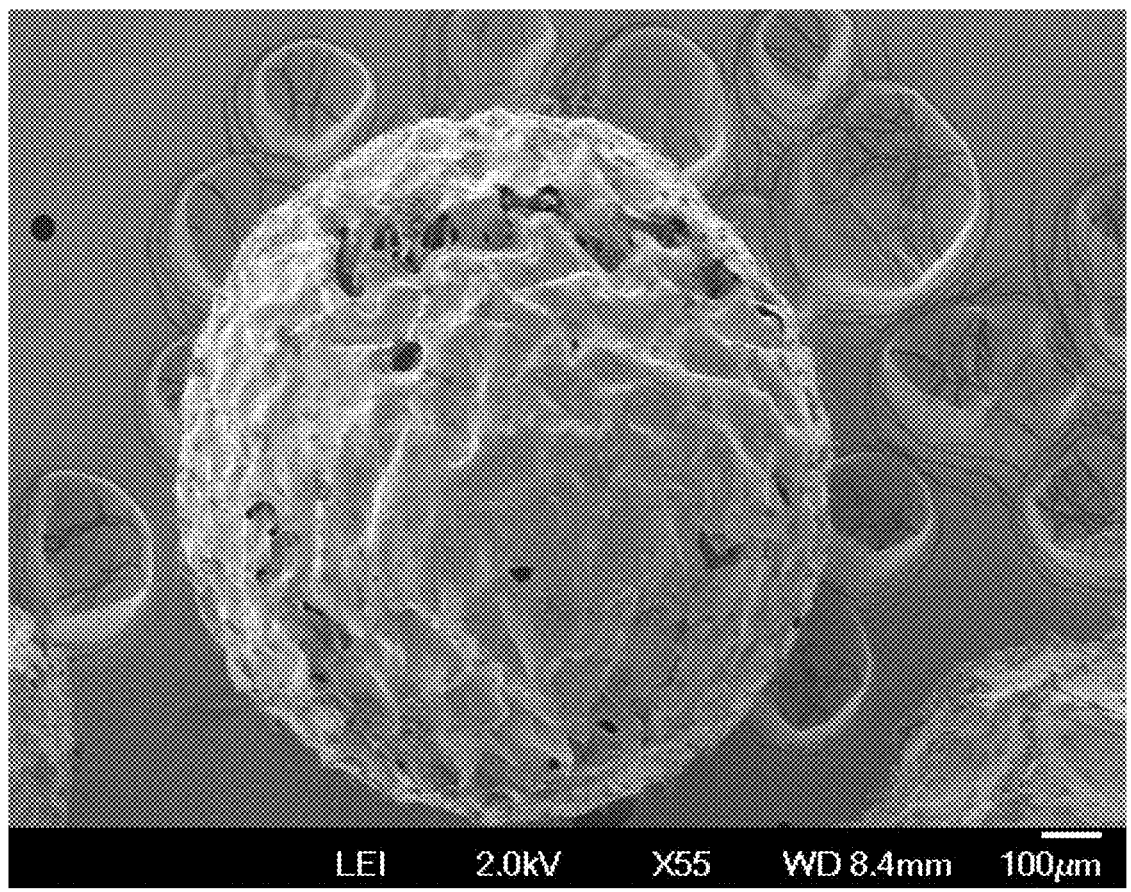
FIG. 3 is an example of a scanning electron microscopy image of an exterior of a microsphere formed in accordance with aspects of this disclosure.

FIG. 3 is an example scanning electron microscopy (SEM) image of an exterior of a microsphere formed in accordance with aspects of this disclosure. Prior to collection of the SEM image, the microsphere was lyophilized. Before lyophilization (freeze drying), saline was removed from the microsphere by rinsing the microsphere repeatedly with deionized water. The resulting microsphere was frozen in liquid nitrogen, and lyophilized to remove any residual water from pores of the microsphere. The SEM image was obtained utilizing a JEOL JSM-6700 SEM (available from JEOL USA, Inc., Peabody, Mass.). FIG. 3 was collected at 55× magnification at 2.0 kilovolts (kV). The microsphere in FIG. 3 had a diameter of about 1100 µm.

Figure 4A:
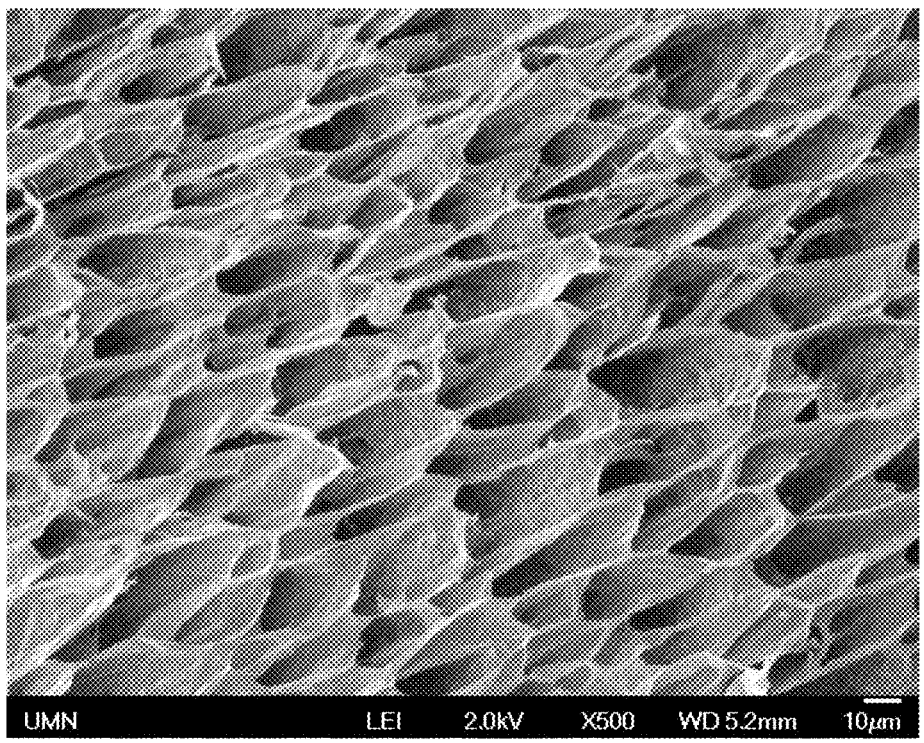
FIGS. 4A and 4B are examples of SEM images of the cross-section of a hydrogel prepared with CCN crosslinked with CMC.
Figure 4B:
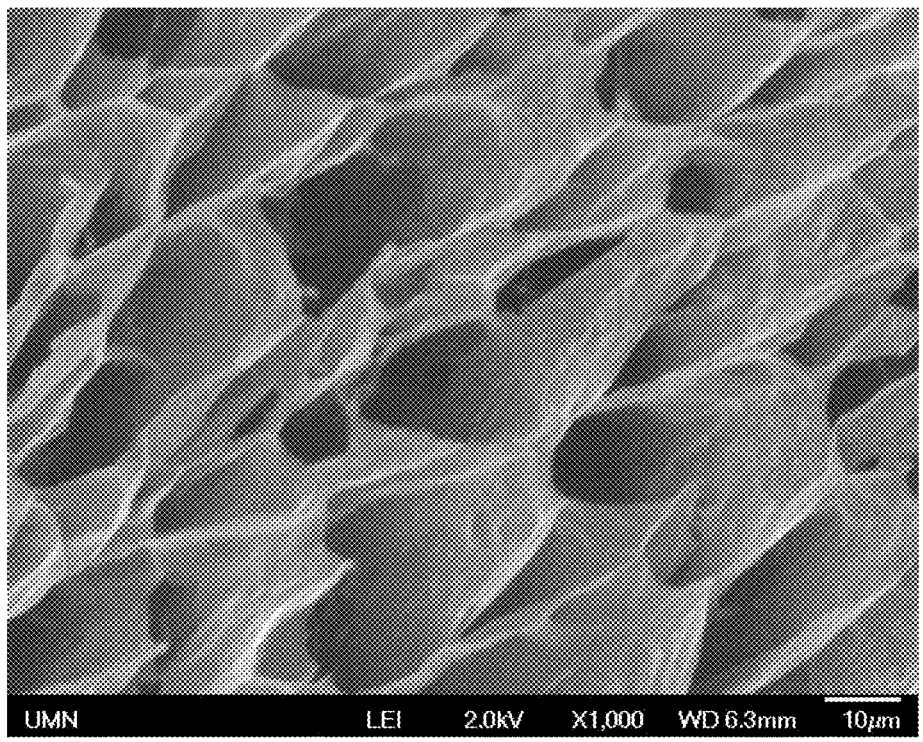

FIGS. 4A and 4B are examples of SEM images of a hydrogel prepared with CCN crosslinked with CMC in accordance with aspects of the disclosure. The hydrogel was cut to expose an interior of the hydrogel and reveal the porous structure of the hydrogel. The SEM images were collected using a JEOL JSM-6700 SEM. FIG. 4A was collected at 500× magnification, while FIG. 4B was collected at 1000× magnification. Because the hydrogel was prepared using CCN crosslinked with CMC, the internal structure of microspheres formed in accordance with this disclosure is expected to be similarly porous.

In some examples, the active ingredient may be loaded into the microspheres during formation of the microspheres, i.e., during the crosslinking of the CCN with the partially oxidized CMC. In such examples, the active ingredient may be deposited into the emulsion along with the CCN and oxidized CMC. As the microspheres form, the active ingredient may load into the microspheres.

In other examples, the active ingredient may be loaded into the microspheres after formation of the microspheres. For example, the microspheres may be immersed in a solution of the active ingredient in a solvent, such as water, to load the active ingredient into the microsphere. In some examples, the active ingredient solution may have a concentration of between about 1 mg active ingredient per mL solvent (mg/mL) and about 2 mg/mL.

In some examples, the active ingredient may be loaded into the microspheres to a concentration of between about 0.3 mg active ingredient per mg dry microsphere (mg/mg) and about 0.75 mg/mg.

FIGS. 5A-5F are light microscopy images illustrating an example of loading a dye (Evan's blue) into microspheres including CCN crosslinked with CMC. FIG. 5A illustrates a plurality of microspheres suspended in normal saline prior to the dye being loaded into the microspheres. Prior to introducing the Evan's blue, saline was removed to the extent practicable using a micropipette, leaving wet microspheres. About 1 mL of a 1% w/v solution of Evan's blue in saline was added to about 50 mg wet microspheres. FIG. 5B was collected about 50 seconds after introducing the Evan's blue solution, and illustrates that loading of the dye into the microspheres has begun. FIG. 5C was taken about 4 minutes after introduction of the Evan's blue solution, and shows that additional dye has been loaded into the microspheres. FIG. 5D was collected about 16 minutes after introduction the Evan's blue solution, and shows further dye uptake by the microspheres. Finally, FIGS. 5E and 5F illustrate microspheres loaded with the dye suspended in normal saline after being removed from the Evan's blue solution.

FIGS. 6A-6C illustrate examples of microspheres according to an aspect of the disclosure after being loaded with various dyes. Specifically, FIG. 6A shows a plurality of microspheres loaded with seafoam green food coloring, FIG. 6B shows a plurality of microspheres loaded with FD&C Red Dye #40, and FIG. 6C shows a plurality of microspheres loaded with FD&C Yellow Dye #5. Prior to collecting the images shown in FIGS. 6A-6C, the microspheres were loaded with the dye in a similar manner to that described above with respect to FIGS. 5A-5F: saline was removed from a suspension of microspheres in saline using a micropipette, and about 1 mL of a 1% w/v solution of the dye in saline was added to about 50 mg wet microspheres. After loading the dye into the microspheres, the remaining dye solution was removed using a micropipette and the dye-loaded microspheres were suspended in saline. FIGS. 5A-5F and 6A-6C illustrate that the microspheres may be loaded with dyes having different functional groups, suggesting that the microspheres may also be loaded with active ingredient that include different functional groups.

Figure 7:
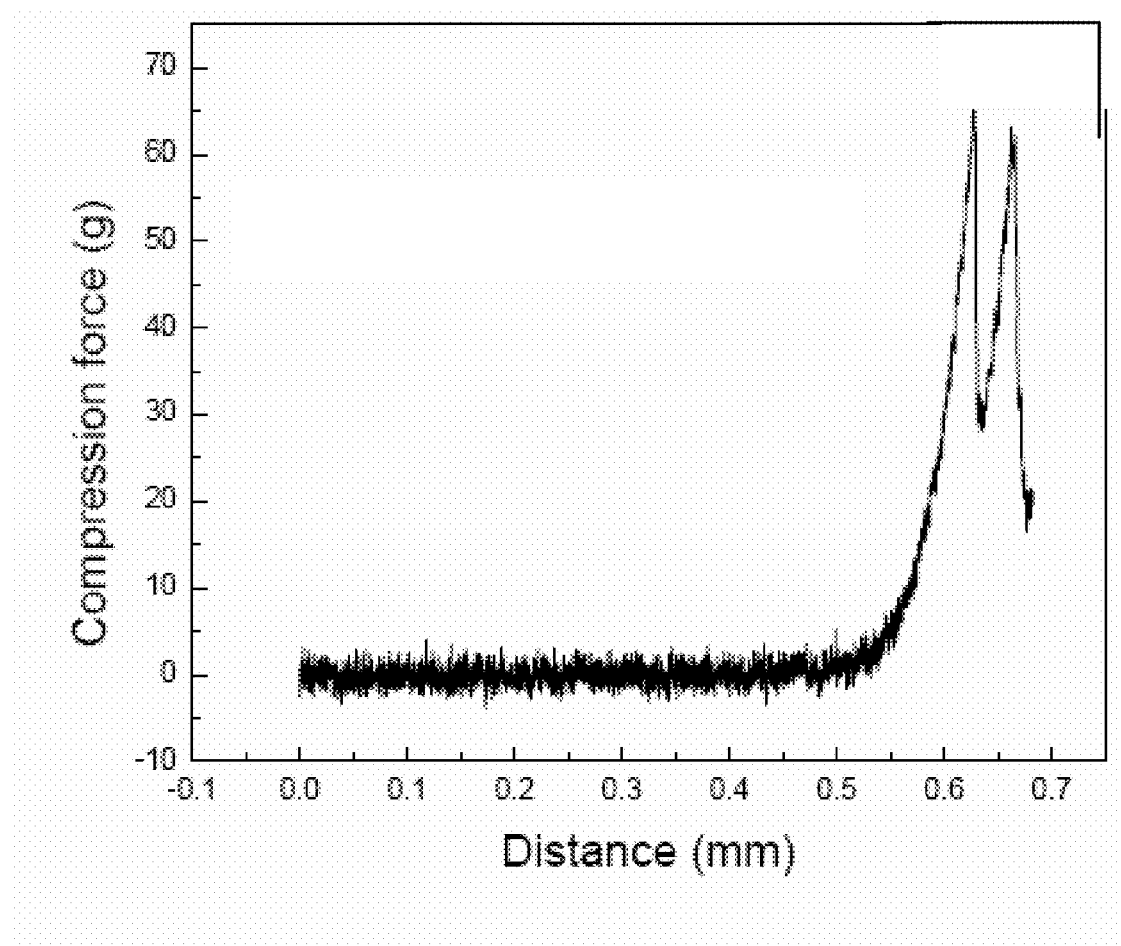
FIG. 7 is an example of a plot of compression force versus distance for a single microsphere having a diameter of about 715 μm.

In some examples, regardless of whether the microspheres are loaded with active agent, the microspheres including CCN crosslinked with CMC may have advantageous mechanical properties. For example, the microspheres may be compressible, and may substantially return to their original shape after being compressed. FIG. 24 is a plot of compression force versus distance for a single microsphere having a diameter of about 715 μm and a crosslinking density of about 10%. The compression test was performed using a TA.XTPlus Texture Analyzer (Texture Technologies Corp., Scarsdale, N.Y.). The microsphere was compressed at a rate of about 0.08 mm/s. As illustrated in FIG. 7, the microsphere compresses about 622 μm (0.622 mm) before irreversibly deforming, resulting in a fracture strain of about 87%. Additionally, the compression force at fracture was about 65.5 g. As described above, the fracture strain may be adjusted between about 70% and about 90% by controlling a crosslinking density between the CCN and CMC.

Figure 8A:
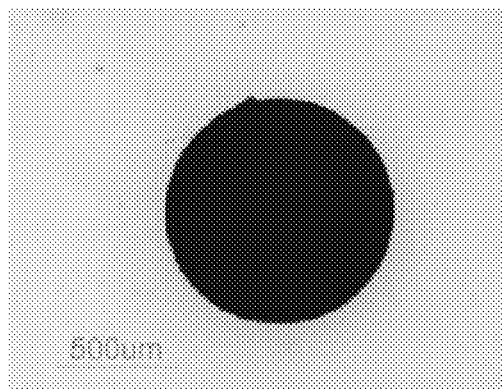
FIGS. 8A-8C are light microscopy images illustrating an example of the compressibility of a microsphere including CCN crosslinked with CMC (dyed with Evan's blue) as the microsphere passes through a polyethylene tube.
Figure 8B:
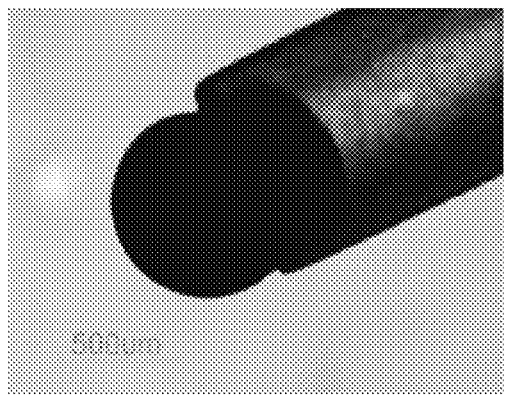
Figure 8C:
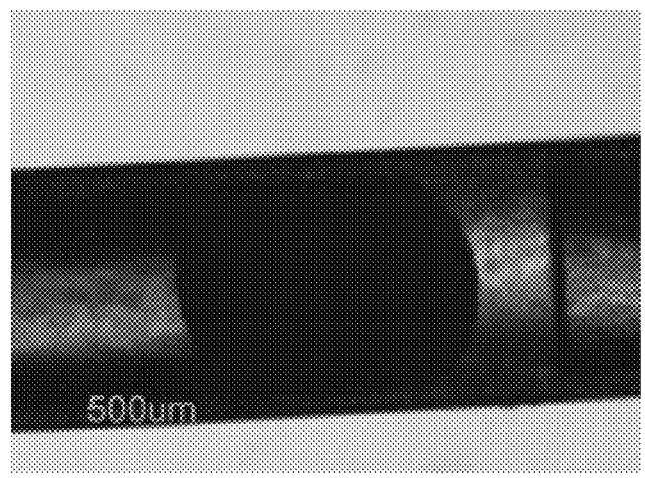

FIGS. 8A-8C are light microscopy images illustrating an example of the compressibility of a microsphere including CCN crosslinked with CMC as the microsphere passes through a polyethylene tube. The microsphere has a diameter of about 925 μm and the catheter has an internal diameter of about 580 μm (PE-50). As FIGS. 8B and 8C illustrate, the microsphere can deform and pass through the internal cavity of the catheter.

Figure 9A:
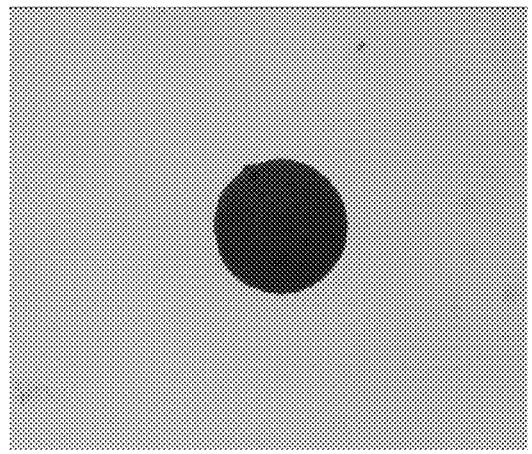
FIGS. 9A-9C are light microscopy images that illustrate another example of the compressibility of a microsphere including CCN crosslinked with CMC (dyed with Evan's blue) as the microsphere passes through a polyethylene tube.
Figure 9B:
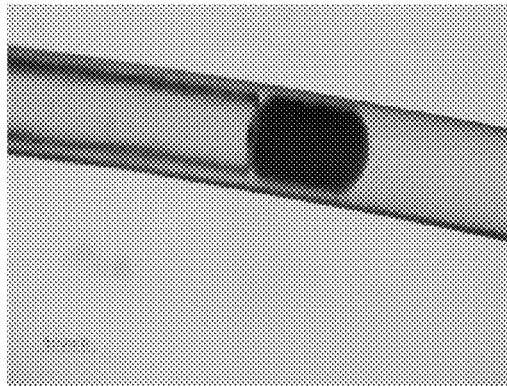
Figure 9C:
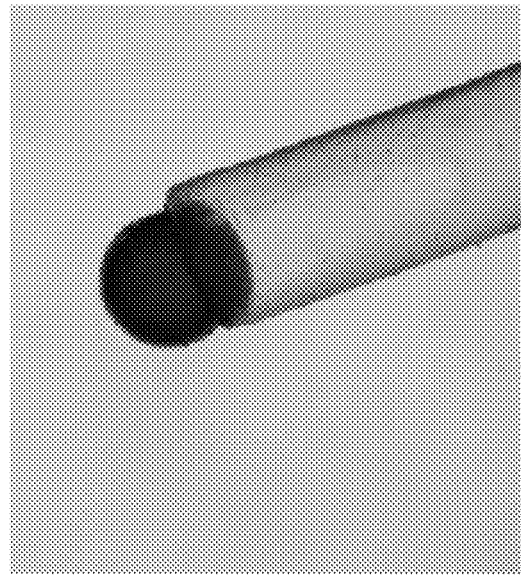

FIGS. 9A-9C are light microscopy images that illustrate another example of the compressibility of a microsphere including CCN crosslinked with CMC and having a diameter of about 860 μm as the microsphere passes through a polyethylene tube. In FIGS. 9A-9C, the catheter again has an internal diameter of about 580 μm (PE-50). As FIGS. 9B and 9C illustrate, the microsphere can reversibly deform, pass through the internal cavity of the catheter, and return to a shape and size substantially similar to the shape and size of the microsphere before passing through the catheter.

Figure 10A:
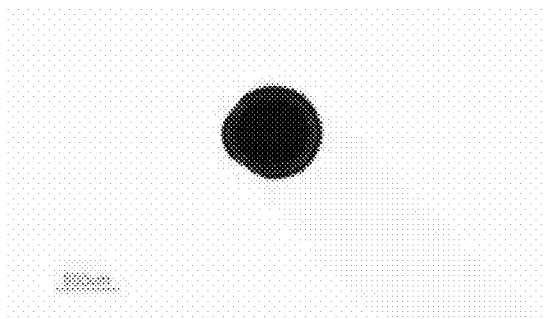
FIGS. 10A and 10B illustrate an example of the resiliency of a microsphere including CCN crosslinked with CMC (dyed with Evan's blue).
Figure 10B:
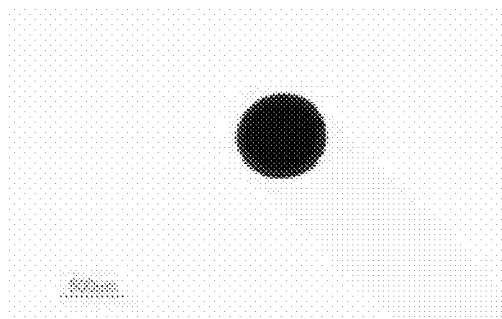

FIGS. 10A and 10B illustrate an example of the resiliency of a microsphere including CCN crosslinked with CMC. The microsphere pictured in FIGS. 10A and 10B has a diameter of about 675 μm and was disposed in a polyethylene tube with an internal diameter of about 580 μm (PE-50) for about 24 hours prior to being released. The image shown in FIG. 10A was collected about 3 seconds after the microsphere was released from the PE tube, and the image shown in FIG. 10B was collected about 5 seconds after the microsphere was released. FIGS. 10A and 10B illustrate that the microsphere may recover its spherical shape and original size relatively quickly after being released from the PE tube.

Figure 11:
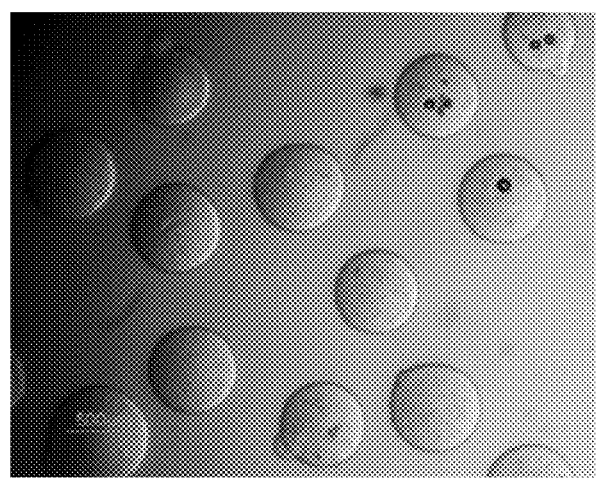
FIG. 11 is a light microscopy image of an example of microspheres including CCN crosslinked with CMC and having diameters between about 500 μm and about 700 μm after being injected through a catheter with an internal diameter of about 667 μm (2 French).

FIG. 11 is a light microscopy image of an example of microspheres having diameters between about 500 μm and about 700 μm taken after the microspheres were injected through a catheter with an internal diameter of about 480 μm (2 French catheter, available from Boston Scientific Corp., Natick, Mass.). As illustrated in FIG. 11, the microspheres substantially retained their original, spherical shape.

Figure 12A:
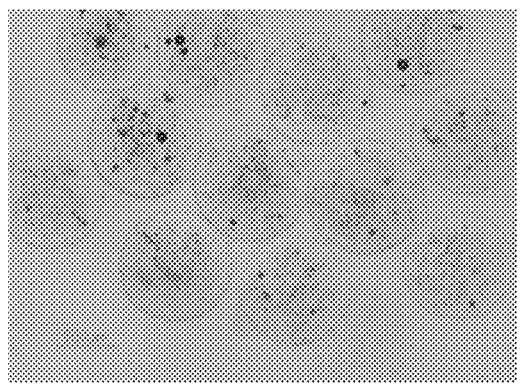
FIGS. 12A and 12B are light microscopy images of an example of microspheres including CCN crosslinked with CMC and having diameters between about 800 μm and about 1000 μm after being injected through a catheter with an internal diameter of about 1 mm (3 French).
Figure 12B:
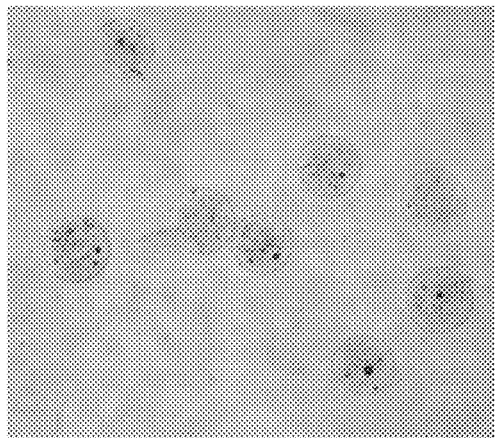

FIGS. 12A and 12B are light microscopy images of an example of microspheres having diameters between about 800 μm and about 1000 μm taken after the microspheres were injected through a catheter with an internal diameter of about 0.53 mm (3 French catheter, Terumo Medical Corp., Somerset, N.J.). As illustrated in FIGS. 12A and 12B, the microspheres substantially retained their original, spherical shape.

Figure 13:
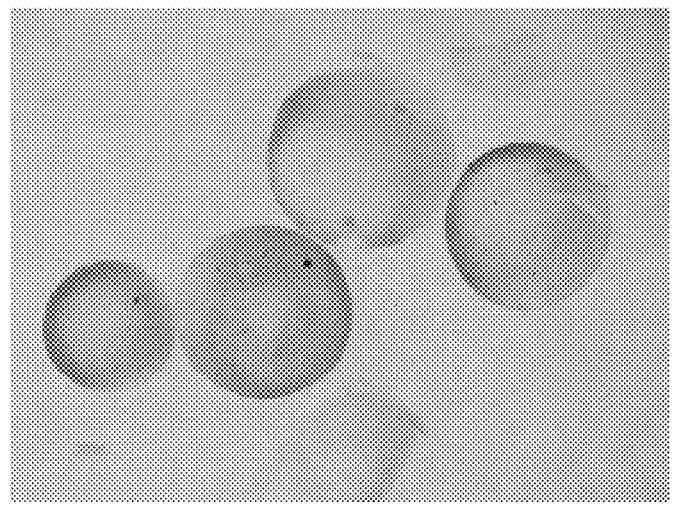
FIG. 13 is a light microscopy image of an example of a plurality of microspheres including CCN crosslinked with CMC after being stored for two months in water.

Microspheres including CCN crosslinked with CMC may be somewhat stable when stored in water, but eventually may begin to degrade. FIG. 13 is a light microscopy image of an example of a plurality of microspheres after being stored for two months in water. The microspheres shown in FIG. 13 had a crosslinking density of about 10%. The microspheres shown in FIG. 13 have been dyed with Evan's blue to increase contrast with the background medium (water). As FIG. 13 illustrates, the microspheres have begun to degrade and show decreased mechanical integrity.

Figure 14A:
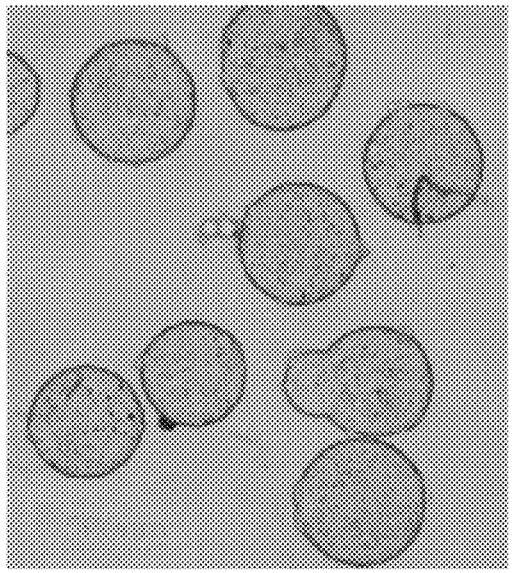
FIGS. 14A-14E are light microscopy images that illustrate an example of a plurality of microspheres including CCN crosslinked with CMC degrading in the presence of lysozyme.
Figure 14B:
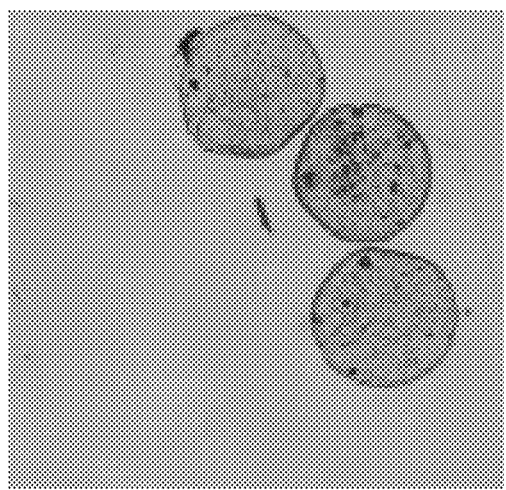
Figure 14C:
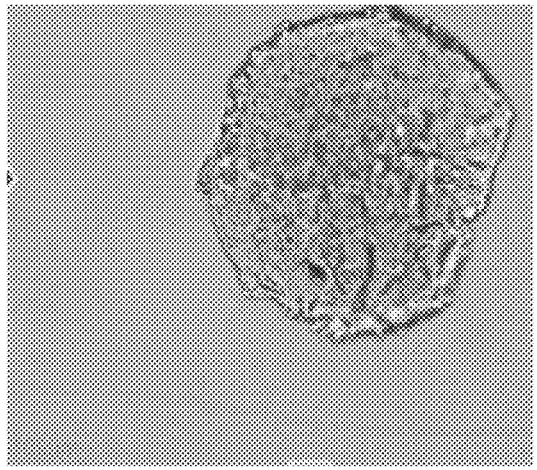
Figure 14D:
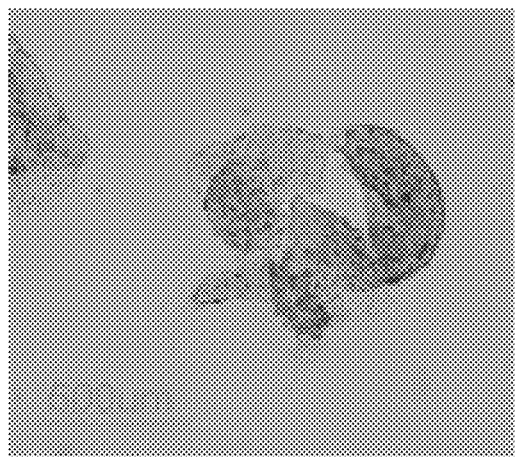
Figure 14E:
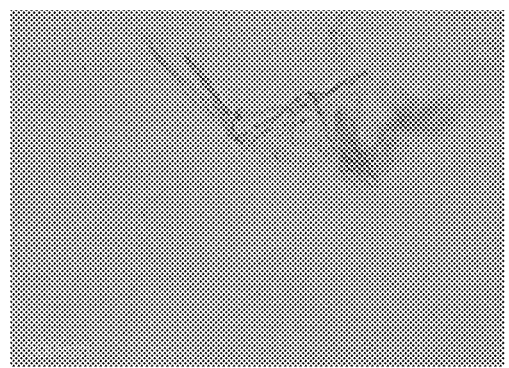

In some examples, microspheres including CCN crosslinked with CMC may degrade more rapidly in the presence of an enzyme such as lysozyme. FIGS. 14A-14E are light microscopy images that illustrate an example of a plurality of microspheres degrading in the presence of lysozyme. The microspheres had a crosslinking density of about 10%. The medium surrounding the microspheres contained 4 mg/mL lysozyme and the microspheres and surrounding medium were kept at a temperature of about 37° C. for the duration of the test. FIG. 14A illustrates the appearance of the microspheres on day 0, soon after the microspheres were placed in the medium. FIG. 14B shows the appearance of the microspheres on day 3. FIG. 14C illustrates the appearance of a microsphere after 7 days. Visual evidence of the beginning of degradation is apparent. FIG. 14D shows the appearance of a microsphere on day 9. Degradation of the microsphere is progressing, mechanical integrity is decreasing, and the microsphere is no longer spherical. Finally, FIG. 14E illustrates the appearance of a microsphere on day 14, at which time pieces of microsphere can be found in the medium, but the microsphere is no longer spherical.

As described above, the degradation time of the microspheres may be adjusted by increasing or decreasing the crosslink density in the microspheres. For example, a higher crosslink density, which may correspond to a higher oxidation degree of the partially oxidized CMC, may lead to an increased degradation time, while a lower crosslink density (a lower oxidation degree of the CMC) may lead to a decreased degradation time.

EXAMPLES

Example 1

Preparation of Partially Oxidized CMC

About 1 g of sodium carboxymethyl cellulose (Sigma-Aldrich, St. Louis, Mo., Mw about 700,000 g/mol) and 80 mL distilled water were added to a 250 mL flask. After the carboxymethyl cellulose dissolved substantially completely, 25% molar equivalent of sodium periodate in 20 mL distilled water was added to the flask. The reaction was allowed to proceed for 24 hours at about 25° C. After 24 hours, about 0.21 g ethylene glycol was added to the flask to stop the reaction. After an additional 30 minutes, the mixture was poured into a dialysis tube (MWCO 3500) to dialyze against distilled water for 3 days. Dry product was obtained by lyophilizing the dialyzed solution. The resulting partially oxidized CMC was labeled OCMC-II.

Example 2

Preparation of Partially Oxidized CMC

About 1 g of sodium carboxymethyl cellulose (Sigma-Aldrich, St. Louis, Mo., Mw about 700,000 g/mol) and 80 mL distilled water were added to a 250 mL flask. After the carboxymethyl cellulose dissolved substantially completely, 10% molar equivalent of sodium periodate in 20 mL distilled water was added to the flask. The reaction was allowed to proceed for 24 hours at about 25° C. After 24 hours, about 0.08 g ethylene glycol was added to the flask to stop the reaction. After an additional 30 minutes, the mixture was poured into a dialysis tube (MWCO 3500) to dialyze against distilled water for 3 days. Dry product was obtained by lyophilizing the dialyzed solution. The resulting partially oxidized CMC was labeled OCMC-I.

Example 3

Preparation of Partially Oxidized CMC

About 1 g of sodium carboxymethyl cellulose (Sigma-Aldrich, St. Louis, Mo., Mw about 700,000 g/mol) and 80 mL distilled water were added to a 250 mL flask. After the carboxymethyl cellulose dissolved substantially completely, 50% molar equivalent of sodium periodate in 20 mL distilled water was added to the flask. The reaction was allowed to proceed for 24 hours at about 25° C. After 24 hours, about 0.42 g ethylene glycol was added to the flask to stop the reaction. After an additional 30 minutes, the mixture was poured into a dialysis tube (MWCO 3500) to dialyze against distilled water for 3 days. Dry product was obtained by lyophilizing the dialyzed solution. The resulting partially oxidized CMC was labeled OCMC-III.

Example 4

Preparation of CCN

In a 3-neck flask, about 2 g chitosan (Sigma-Aldrich, St. Louis, Mo., greater than 75% deacetylated) was added to a mixture of about 16 g sodium hydroxide, about 20 mL distilled water, and about 20 mL isopropanol. The mixture was stirred at about 25° C. for about 24 hours. Before carboxymethylation, the flask was maintained in a water bath at about 50° C. for about 1 hour. About 16 g monochloroacetic acid (Sigma-Aldrich, St. Louis, Mo.) in 10 mL isopropanol then was added dropwise into the reaction mixture. The reaction mixture was stirred at about 50° C. for an additional 4 hrs, and the reaction was stopped by adding about 80 mL of 70% ethanol. The precipitate was filtered and rinsed thoroughly with 70-90% ethanol and vacuum dried at room temperature.

The dried product was dissolved in about 100 mL water and homogenized for 2 hours. Any insoluble residue present in the mixture was removed by centrifuging. The supernatant was dialyzed in an MWCO 3500 dialysis tube against distilled water and then lyophilized. The resulting CCN was labeled CCN-I.

Example 5

Preparation of CCN

In a 3-neck flask, about 2 g chitosan (Sigma-Aldrich, St. Louis, Mo., greater than 75% deacetylated) was added to a mixture of about 8 g sodium hydroxide, about 10 mL distilled water, and about 10 mL isopropanol. The mixture was stirred at room temperature for about 24 hours. Before carboxymethylation, the flask was maintained in a water bath at about 50° C. for about 1 hour. About 8 g monochloroacetic acid (Sigma-Aldrich, St. Louis, Mo.) in 5 mL isopropanol then was added dropwise into the reaction mixture. The reaction mixture was stirred at about 50° C. for an additional 4 hrs, and the reaction was stopped by adding about 80 mL of 70% ethanol. The precipitate was filtered and rinsed thoroughly with 70-90% ethanol and vacuum dried at room temperature.

The dried product was dissolved in about 100 mL water and homogenized for 2 hours. Any insoluble residue present in the mixture was removed by centrifuging. The supernatant was dialyzed in an MWCO 3500 dialysis tube against distilled water and then lyophilized. The resulting CCN was labeled CCN-II.

Example 6

Preparation of CCN

In a 3-neck flask, about 2 g chitosan (Sigma-Aldrich, St. Louis, Mo., greater than 75% deacetylated) was added to a mixture of about 8 g sodium hydroxide, about 8 mL distilled water, and about 32 mL isopropanol. The mixture was stirred for about 24 hours at about 25° C. Before carboxymethylation, the flask was maintained in a water bath at about 50° C. for about 1 hour. About 16 g monochloroacetic acid (Sigma-Aldrich, St. Louis, Mo.) in 10 mL isopropanol then was added dropwise into the reaction mixture. The reaction mixture was stirred at about 50° C. for an additional 4 hrs, and the reaction was stopped by adding about 80 mL of 70% ethanol. The precipitate was filtered and rinsed thoroughly with 70-90% ethanol and vacuum dried at room temperature.

The dried product was dissolved in about 100 mL water and homogenized for 2 hours. Any insoluble residue present in the mixture was removed by centrifuging. The supernatant was dialyzed in an MWCO 3500 dialysis tube against distilled water and then lyophilized. The resulting CCN was labeled CCN-III.

Example 7

Preparation of CCN and CMC Microspheres

About 0.075 g of CCN-I was mixed in about 5 mL of water to form a 1.5% w/v CCN-I solution. Similarly, about 0.075 g OCMC-I was mixed in about 5 ml water to form a 1.5% w/v OCMC-I solution. The CCN-I and OCMC-I solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope, was about 515±3 µm.

Example 8

Preparation of CCN and CMC Microspheres

About 0.075 g of CCN-I was mixed in about 5 mL of water to form a 1.5% w/v CCN-I solution. Similarly, about 0.075 g OCMC-II was mixed in about 5 ml water to form a 1.5% w/v OCMC-I solution. The CCN-I and OCMC-II solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope, was about 594±3 µm.

Example 9

Preparation of CCN and CMC Microspheres

About 0.075 g of CCN-I was mixed in about 5 mL of water to form a 1.5% w/v CCN-I solution. Similarly, about 0.075 g OCMC-III was mixed in about 5 ml water to form a 1.5% w/v OCMC-I solution. The CCN-I and OCMC-III solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope was about 702±3 µm.

Example 10

Preparation of CCN and CMC Microspheres

About 0.1 g of CCN-II was mixed in about 5 mL of water to form a 2% w/v CCN-I solution. Similarly, about 0.1 g OCMC-II or 0.1 OCMC-III was mixed in about 5 ml water to form a 2% w/v OCMC-II solution or a 2% w/v OCMC-III solution. The CCN-I and OCMC-I solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope was about 2000 µm.

Example 11

Microspheres including CMC crosslinked with CCN were prepared in accordance with the techniques described herein to have diameters between about 300 µm and about 500 µm. In particular, in a 22 mL glass vial, a solution including 2.5% weight per volume CCN in 5 mL of water was mixed with a solution including 2.5% weight per volume partially oxidized CMC in 5 mL of water. The mixture of CCN and partially oxidized CMC in water was then added to 50 mL mineral oil containing 0.1 mL Span 80. The emulsion was mixed for about 15 minutes at 550 rpm and room temperature. After 15 minutes, the emulsion was heated at a temperature of about 37° C. for about 30 minutes with continued stirring. An additional 0.6 mL Span® 80 was added to the emulsion. The emulsion was then heated at about 48° C. for about 16 hours with continued stirring. The sediment in the emulsion was then isolated by filtration to remove the oil phase. The resulting microspheres were rinsed with 5% TWEEN® 80 in water, then with normal saline. Microspheres with a diameter between 300 and 500 µm were obtained by manual sieving. The microspheres were stored in saline at between 2 and 8° C.

Figure 15:
FIG. 15 is a photograph of microspheres including CCN crosslinked with CMC mixed in an example hand soap, an example acne cleanser, an example body wash, an example toothpaste, and an example shave gel.
Figure 16C:
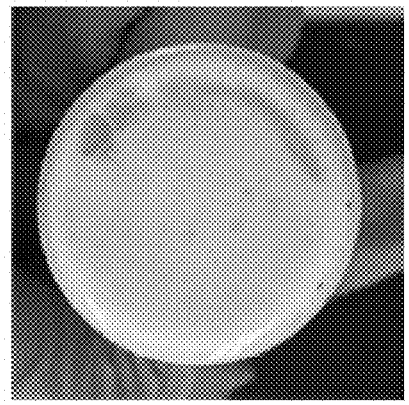
FIGS. 16A-16E are photographs of microspheres including CCN crosslinked with CMC mixed in an example hand soap, an example acne cleanser, an example body wash, an example toothpaste, and an example shave gel about 30 minutes after mixing.
Figure 16B:
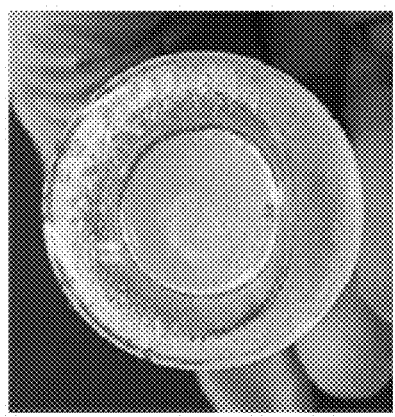
Figure 16A:
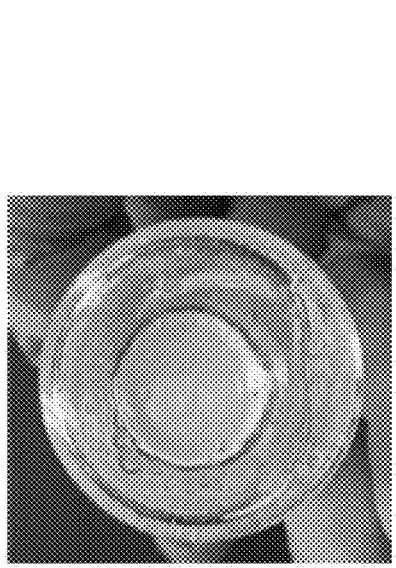
Figure 16E:
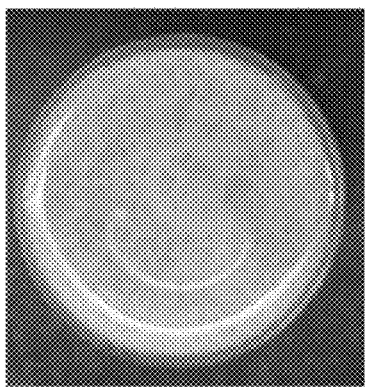
Figure 16D:
Figure 17C:
FIGS. 17A-17E are photographs of microspheres including CCN crosslinked with CMC mixed in an example hand soap, an example acne cleanser, an example body wash, an example toothpaste, and an example shave gel about 12 days after mixing.
Figure 17B:
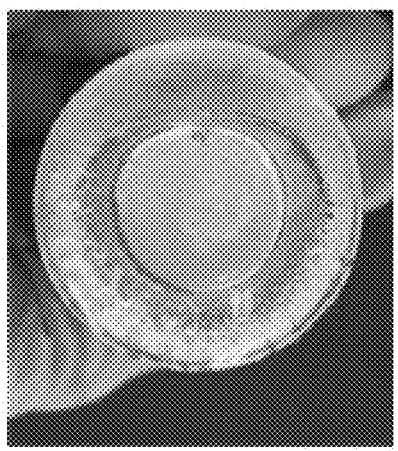
Figure 17A:
Figure 17E:
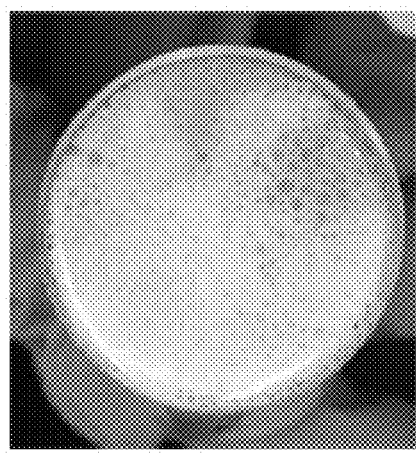
Figure 17D:
Figure 20A:
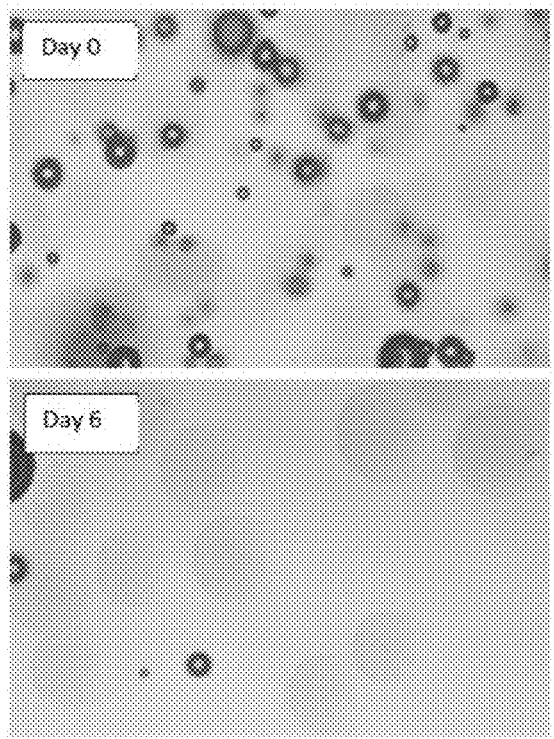
FIGS. 20A-20D are optical micrographs of microspheres including CCN crosslinked with CMC mixed in an example acne cleanser at 30 minutes after mixing, about 5 days after mixing, about 6 days after mixing, and about 11 days after mixing, respectively.
Figure 20B:
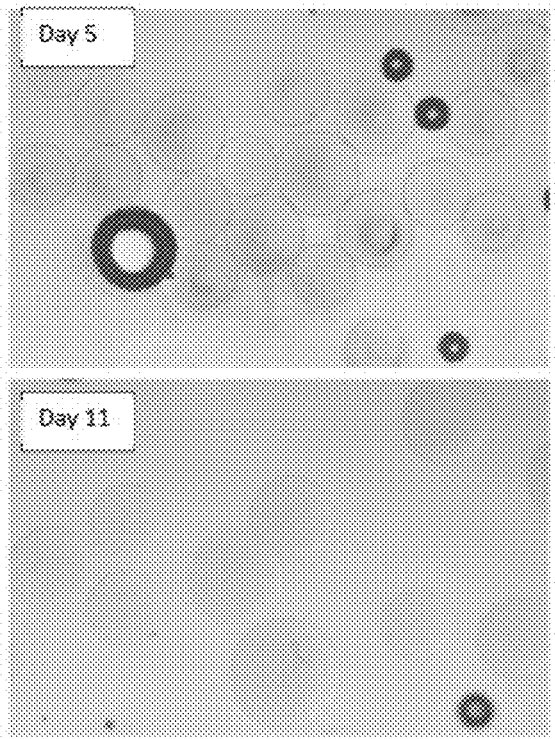
Figure 20C:
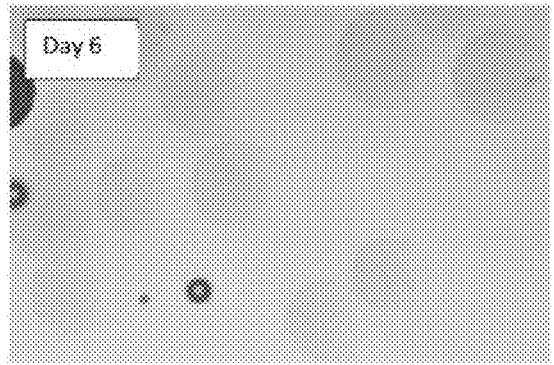
Figure 20D:
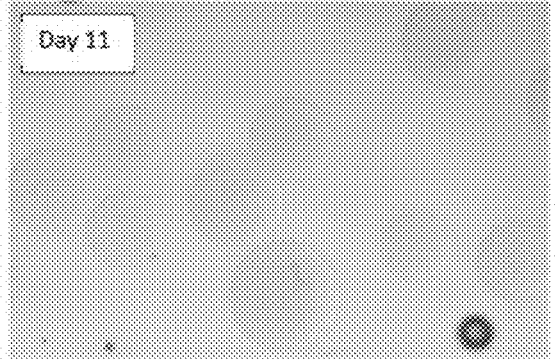

About 0.1 mg of wet microspheres were deposited in each of five 20 mL glass vials. About 1 mL of personal care product was added to each respective vial. The respective personal care products were Dial® hand soap (available from The Dial Corporation, Rocky Hill, Conn.); Well at Wallgreens® acne foaming wash (available from Walgreens Co., Deerfield, Ill.); Dove® body wash (available from Unilever North America, Englewood Cliffs, N.J.); Colgate® toothpaste (available from Colgate-Palmolive Co., New York City, N.Y.); and Studio 35 Men's shave gel (available from Walgreens Co., Deerfield, Ill.). The respective combinations were well mixed. FIG. 15 is a photograph of microspheres mixed in, from left to right, the Dial® hand soap, the Well at Wallgreens® acne foaming wash, the Dove® body wash, the Colgate® toothpaste, and the Studio 35 Men's shave gel. The mixtures were stored at room temperature after mixing.

FIGS. 16A-16E are photographs of microspheres including CMC crosslinked with CCN mixed in the Dial® hand soap, the Well at Wallgreens® acne foaming wash, the Dove® body wash, the Colgate® toothpaste, and the Studio 35 Men's shave gel, respectively, about 30 minutes after mixing. FIGS. 17A-17E are photographs of microspheres including CMC crosslinked with CCN mixed in the Dial® hand soap, the Well at Wallgreens® acne foaming wash, the Dove® body wash, the Colgate® toothpaste, and the Studio 35 Men's shave gel, respectively, about 12 days after mixing. As shown in FIGS. 17A-17E compared to FIGS. 16A-16E, the appearance of the mixtures did not change significantly over the 12 days. The microspheres were will suspended in the body wash, the toothpaste, and the shave gel throughout the study period, but settled out of the facial wash and the hand wash due to the relatively low viscosity or density of the facial wash and the hand wash.

FIG. 18 is an optical micrograph of microspheres including CMC crosslinked with CCN in normal saline (0.9% NaCl).

FIGS. 19A-19D are optical micrographs of microspheres including CCN crosslinked with CMC mixed in the Dial® hand soap at 30 minutes after mixing, about 5 days after mixing, about 6 days after mixing, and about 11 days after mixing, respectively. The micrographs were collected with the microspheres still mixed in the hand soap. As shown in FIGS. 19A-19D, the microspheres maintained their spherical shape throughout the duration of the observation, and did not significantly change in size.

FIGS. 20A-20D are optical micrographs of microspheres including CCN crosslinked with CMC mixed in Well at Wallgreens® acne foaming wash at 30 minutes after mixing, about 5 days after mixing, about 6 days after mixing, and about 11 days after mixing, respectively. The micrographs were collected with the microspheres still mixed in the acne foaming wash. As shown in FIGS. 20A-20D, the microspheres maintained their spherical shape throughout the duration of the observation, and did not significantly change in size.

FIGS. 21A and 21B are optical micrographs of microspheres including CCN crosslinked with CMC mixed in Studio 35 Men's shave gel at 30 minutes after mixing and about 6 days after mixing, respectively. The micrographs were collected after the microspheres were washed thoroughly in normal saline. As shown in FIGS. 21A and 21B, the microspheres maintained their spherical shape throughout the duration of the observation, and did not significantly change in size.

FIGS. 22A-22C are optical micrographs of microspheres including CCN crosslinked with CMC mixed in the Colgate® toothpaste at 30 minutes after mixing, about 6 days after mixing, and about 12 days after mixing, respectively. The micrographs were collected after the microspheres were washed thoroughly in normal saline. As shown in FIGS. 22A-22C, the microspheres maintained their spherical shape throughout the duration of the observation, and did not significantly change in size.

FIGS. 23A-23D are optical micrographs of microspheres including CCN crosslinked with CMC mixed in the Dove® body wash at 30 minutes after mixing, about 5 days after mixing, about 6 days after mixing, and about 11 days after mixing, respectively. The micrographs were collected after the microspheres were washed thoroughly in normal saline. As shown in FIGS. 23A-23D, the microspheres maintained their spherical shape throughout the duration of the observation, and did not significantly change in size.

Various examples have been described. These and other examples are within the scope of the following claims.

What is claimed is:

1. A personal care product comprising:
    a plurality of microspheres comprising carboxymethyl chitosan crosslinked with carboxymethyl cellulose, wherein the plurality of microspheres has an average diameter between about 40 micrometers and about 2200 micrometers; and
    an active ingredient, wherein the active ingredient comprises at least one of an antibiotic, an antibacterial agent, an antimicrobial, an antifungal, or a pain relief active ingredient.

2. The personal care product of claim 1, wherein the plurality of microspheres is substantially free of a small molecule crosslinking agent, and wherein the plurality of microspheres is biodegradable.

3. The personal care product of claim 1, further comprising at least one of water, a thickener, a surfactant, a pH adjusting agent, a moisturizer, or a preservative.

4. The personal care product of claim 1, wherein the personal care product is a toothpaste, the toothpaste comprising:
    a base material comprising at least one of a fluoride source or a surfactant;
    the plurality of microspheres comprising carboxymethyl chitosan crosslinked with carboxymethyl cellulose; and
    the active ingredient, wherein the active ingredient comprises the antibacterial agent.

5. The personal care product of claim 4, wherein the base material further comprises at least one of a flavorant, a remineralizer, a compound to reduce sensitivity, or a sugar alcohol.

6. The personal care product of claim 4, wherein the plurality of microspheres is substantially free of a small molecule crosslinking agent, and wherein the plurality of microspheres is biodegradable.

7. The personal care product of claim 1, wherein the personal care product is an acne cleanser, the acne cleanser comprising:
    the plurality of microspheres comprising carboxymethyl chitosan crosslinked with carboxymethyl cellulose;
    the active ingredient, wherein the active ingredient comprises the antimicrobial; and
    a second active ingredient comprising at least one of salicylic acid, benzoyl peroxide, or a sulfur compound.

8. The personal care product of claim 7, further comprising a surfactant comprising at least one of a nonionic surfactant, an anionic surfactant, a cationic surfactant, or an amphoteric surfactant; and at least one of an alcohol, a moisturizer, a thickener, a chelating agent, a pH adjuster, or an oil.

9. The personal care product of claim 7, wherein the plurality of microspheres is substantially free of a small molecule crosslinking agent, and wherein the plurality of microspheres is biodegradable.

10. The personal care product of claim 1, wherein the personal care product is a body wash or facial wash, the body wash or facial wash comprising:
    a surfactant;
    the plurality of microspheres comprising carboxymethyl chitosan crosslinked with carboxymethyl cellulose; and
    the active ingredient, wherein the active ingredient comprises the antibacterial or the antifungal.

11. The personal care product of claim 10, wherein the surfactant comprises at least one of a nonionic surfactant, an anionic surfactant, a cationic surfactant, or an amphoteric surfactant.

12. The personal care product of claim 10, further comprising at least one of a moisturizer, a thickener, or a preservative.

13. The personal care product of claim 10, wherein the plurality of microspheres is substantially free of a small molecule crosslinking agent, and wherein the plurality of microspheres is biodegradable.

14. The personal care product of claim 1, wherein the personal care product is a soap, the soap comprising:
    a derivative of a fatty acid;
    the plurality of microspheres comprising carboxymethyl chitosan crosslinked with carboxymethyl cellulose; and
    the active ingredient, wherein the active ingredient comprises the antibacterial or the antifungal.

15. The personal care product of claim 14, further comprising a surfactant comprising at least one of a nonionic surfactant, an anionic surfactant, a cationic surfactant, or an amphoteric surfactant; and at least one of a moisturizer, a thickener, or a preservative.

16. The personal care product of claim 14, wherein the plurality of microspheres is substantially free of a small molecule crosslinking agent, and wherein the plurality of microspheres is biodegradable.

17. The personal care product of claim 1, wherein the personal care product is a topical pain relief product, the topical pain relief product comprising:
    the active ingredient, wherein the active ingredient comprises the pain relief active ingredient, and wherein the pain relief active ingredient comprises at least one of an anesthetic, a pain reliever, an anti-inflammatory agent, or an analgesic; and
    the plurality of microspheres comprising carboxymethyl chitosan crosslinked with carboxymethyl cellulose.

18. The personal care product of claim 17, wherein the pain relief active ingredient comprises at least one of capsaicin, a salicylate, hydrocortisone, menthol, methylsalicylate, camphor, or pramoxine.

19. The personal care product of claim 17, further comprising at least one of a surfactant, water, a thickener, a pH adjusting agent, a moisturizer, or a preservative.

20. The personal care product of claim 17, wherein the active ingredient is loaded in the plurality of microspheres.

21. The personal care product of claim 17, wherein the plurality of microspheres is substantially free of a small molecule crosslinking agent, and wherein the plurality of microspheres are biodegradable.

22. The personal care product of claim 1, wherein the personal care product is a topical antibiotic product, the topical antibiotic product comprising:
   the active ingredient, wherein the active ingredient comprises at least one of the antibiotic, the antimicrobial, or the antifungal; and
   the plurality of microspheres comprising carboxymethyl chitosan crosslinked with carboxymethyl cellulose.

23. The personal care product of claim 22, wherein the at least one of the antibiotic, the antimicrobial, or the antifungal comprises at least one of bacitracin, neomycin, or polymyxin B.

24. The personal care product of claim 22, further comprising at least one of water, a thickener, a surfactant, a pH adjusting agent, a moisturizer, a preservative, or an analgesic.

25. The personal care product of claim 22, wherein the at least one of the antibiotic, the antimicrobial, or the antifungal is loaded in the plurality of microspheres.

26. The personal care product of claim 22, wherein the plurality of microspheres is substantially free of a small molecule crosslinking agent, and wherein the plurality of microspheres are biodegradable.

* * * * *